(12) United States Patent
Androulaki et al.

(10) Patent No.: US 12,010,244 B2
(45) Date of Patent: Jun. 11, 2024

(54) BLOCKCHAIN BASED VERIFIABILITY OF USER STATUS

(71) Applicant: International Business Machines Corporation, Armonk, NY (US)

(72) Inventors: Elli Androulaki, Zürich (CH); Alessandro Sorniotti, Rueschlikon (CH); Ilie Circiumaru, Rueschlikon (CH); Miguel Angel Prada Delgado, Rueschlikon (CH); Marc Ph. Stoecklin, Rueschlikon (CH); Marko Vukolić, Rueschlikon (CH); Jesus Diaz Vico, Rüschlikon (CH)

(73) Assignee: International Business Machines Corporation, Armonk, NY (US)

( * ) Notice: Subject to any disclaimer, the term of this patent is extended or adjusted under 35 U.S.C. 154(b) by 649 days.

(21) Appl. No.: 17/093,037

(22) Filed: Nov. 9, 2020

(65) Prior Publication Data
US 2022/0150073 A1 May 12, 2022

(51) Int. Cl.
*H04L 29/06* (2006.01)
*G06K 7/10* (2006.01)
(Continued)

(52) U.S. Cl.
CPC ........ *H04L 9/3247* (2013.01); *G06K 7/10722* (2013.01); *G06K 7/1417* (2013.01);
(Continued)

(58) Field of Classification Search
CPC . H04L 9/3247; H04L 9/14; H04L 9/30; H04L 9/3226; H04L 9/3263; H04L 9/50;
(Continued)

(56) References Cited

U.S. PATENT DOCUMENTS 8,244,699 B2 * 8/2012 Bolohan ............... G06F 16/213
707/806
8,689,287 B2 * 4/2014 Bohmer ............... H04L 9/3234
726/8

(Continued)

FOREIGN PATENT DOCUMENTS

CN 106911470 A * 6/2017 ........... G06Q 20/023
CN 110278211 A * 9/2019 ............. H04L 63/12
(Continued)

OTHER PUBLICATIONS

Hasan et al. "Blockchain-based Solution for COVID-19 Digital Medical Passports and Immunity Certificates." techrxiv.org , Aug. 14, 2020.
(Continued)

*Primary Examiner* — Sher A Khan

(57) ABSTRACT

An example operation may include one or more of extracting a data object from a machine-readable code. The data object can include fields of data signed with a digital signature of a private key, detecting an identifier of an issuer of the data object from the extracted data object, retrieving a public key from a blockchain based on the identifier of the issuer detected from the field of the extracted data object, and verifying the digital signature of the private key based on the fetched public key.

20 Claims, 22 Drawing Sheets

(51) Int. Cl.
    *G06K 7/14*     (2006.01)
    *G06K 19/06*     (2006.01)
    *G16H 10/40*     (2018.01)
    *G16H 10/60*     (2018.01)
    *H04L 9/14*     (2006.01)
    *H04L 9/30*     (2006.01)
    *H04L 9/32*     (2006.01)

(52) U.S. Cl.
    CPC ....... *G06K 19/06037* (2013.01); *G16H 10/40* (2018.01); *G16H 10/60* (2018.01); *H04L 9/14* (2013.01); *H04L 9/30* (2013.01)

(58) Field of Classification Search
    CPC ............ H04L 2209/88; G06K 7/10722; G06K 7/1417; G06K 19/06037; G06K 7/1095; G16H 10/40; G16H 10/60; G16H 50/80; G16H 10/65; G09G 5/00
    See application file for complete search history.

(56) References Cited

U.S. PATENT DOCUMENTS

| | | | | |
|---|---|---|---|---|
| 9,418,052 | B2* | 8/2016 | Shelby | G06F 40/143 |
| 9,483,245 | B2* | 11/2016 | Asayag | G06F 16/00 |
| 10,250,395 | B1* | 4/2019 | Borne-Pons | H04L 9/3247 |
| 10,467,468 | B2* | 11/2019 | Livesay | H04W 12/02 |
| 10,832,214 | B1* | 11/2020 | Leise | G07C 5/0808 |
| 10,943,680 | B1* | 3/2021 | Knas | H04L 9/0861 |
| 2004/0059744 | A1* | 3/2004 | Duncan | G16H 10/40 |
| | | | | 707/999.102 |
| 2006/0242184 | A1* | 10/2006 | Shur | G06F 16/9024 |
| | | | | 707/E17.118 |
| 2014/0254796 | A1* | 9/2014 | Li | H04L 9/3263 |
| | | | | 380/246 |
| 2014/0351686 | A1* | 11/2014 | Yawn | G06F 40/186 |
| | | | | 715/230 |
| 2016/0342978 | A1* | 11/2016 | Davis | G06Q 20/0655 |
| 2017/0091388 | A1* | 3/2017 | Zolla | G16H 10/60 |
| 2019/0260593 | A1* | 8/2019 | Bisti | H04L 9/3247 |
| 2020/0035339 | A1* | 1/2020 | Eevani | H04L 9/0847 |
| 2020/0081899 | A1* | 3/2020 | Shapur | G06F 16/211 |
| 2020/0127828 | A1* | 4/2020 | Liu | H04L 9/0637 |
| 2020/0211409 | A1* | 7/2020 | Latorre | G09B 19/00 |
| 2020/0220726 | A1* | 7/2020 | Lougheed, III | G06F 16/211 |
| 2020/0341951 | A1* | 10/2020 | Oberhofer | G06F 16/254 |
| 2020/0358600 | A1* | 11/2020 | Xu | H04L 9/3231 |
| 2020/0366484 | A1* | 11/2020 | So | H04L 9/3213 |
| 2021/0027293 | A1* | 1/2021 | Groarke | H04L 63/123 |
| 2021/0191903 | A1* | 6/2021 | Shetty | G06F 16/128 |
| 2022/0138181 | A1* | 5/2022 | Irazabal | G06F 16/2379 |
| | | | | 707/703 |
| 2022/0358185 | A1* | 11/2022 | Newman | G06F 16/211 |

FOREIGN PATENT DOCUMENTS

| | | | | |
|---|---|---|---|---|
| CN | 112347521 A | * | 2/2021 | |
| DE | 102017205165 A1 | * | 9/2018 | .......... G06F 21/645 |
| EP | 2747369 A1 | | 6/2014 | |
| EP | 3422221 A1 | | 1/2019 | |
| EP | 3627253 A1 | * | 3/2020 | .......... G05B 19/408 |
| EP | 3632034 B1 | * | 10/2021 | .......... H04L 9/0825 |
| GB | 2600140 A | * | 4/2022 | ............. G06F 21/62 |
| WO | 2009070430 A2 | | 6/2009 | |
| WO | WO-2018026360 A1 | * | 2/2018 | ............. G06F 21/44 |
| WO | 2018039312 A1 | | 3/2018 | |
| WO | WO-2018052914 A1 | * | 3/2018 | .......... G06F 16/958 |
| WO | WO-2020041127 A1 | * | 2/2020 | ........ G06F 16/1837 |
| WO | WO-2021077118 A1 | * | 4/2021 | ............. G06F 21/31 |

OTHER PUBLICATIONS

Khurshid "Applying Blockchain Technology to Address the Crisis of Trust During the COVID-19 Pandemic." JMIR Medical Informatics 8.9, published online Sep. 22, 2020.

Onik et al., et al. "Privacy Protection And Management Of Medical Records Using Blockchain Technology." Big Data Analytics for Intelligent Healthcare Management, Elsevier, Apr. 2019.

* cited by examiner

FIG. 1A
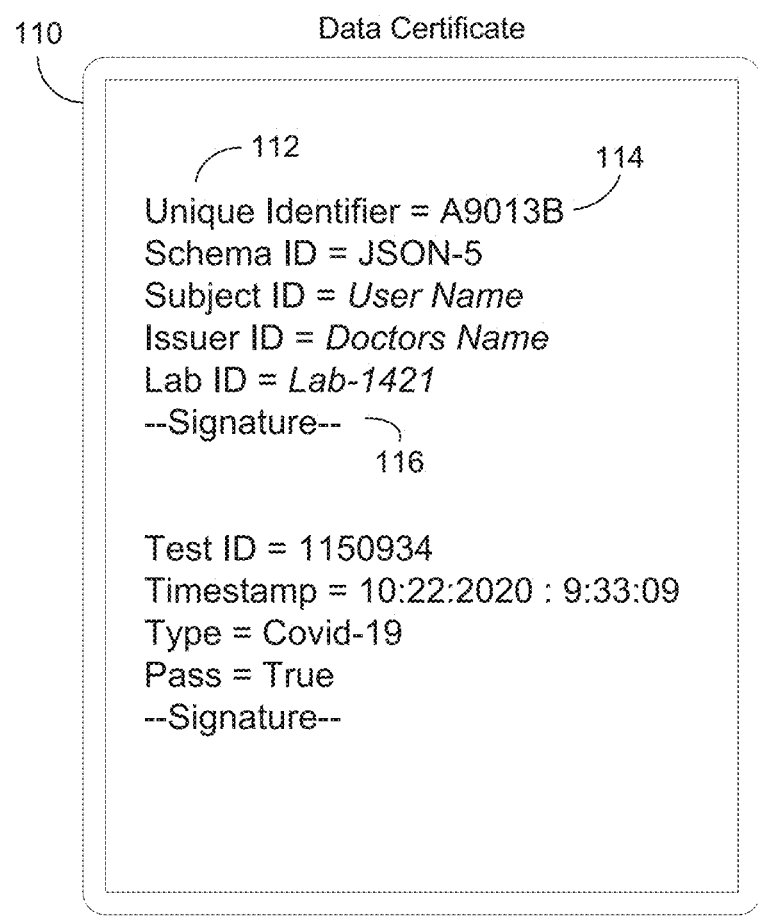
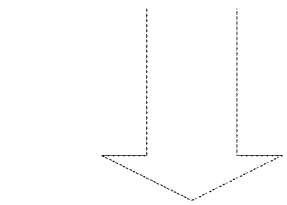
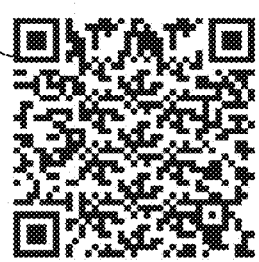
QR Code

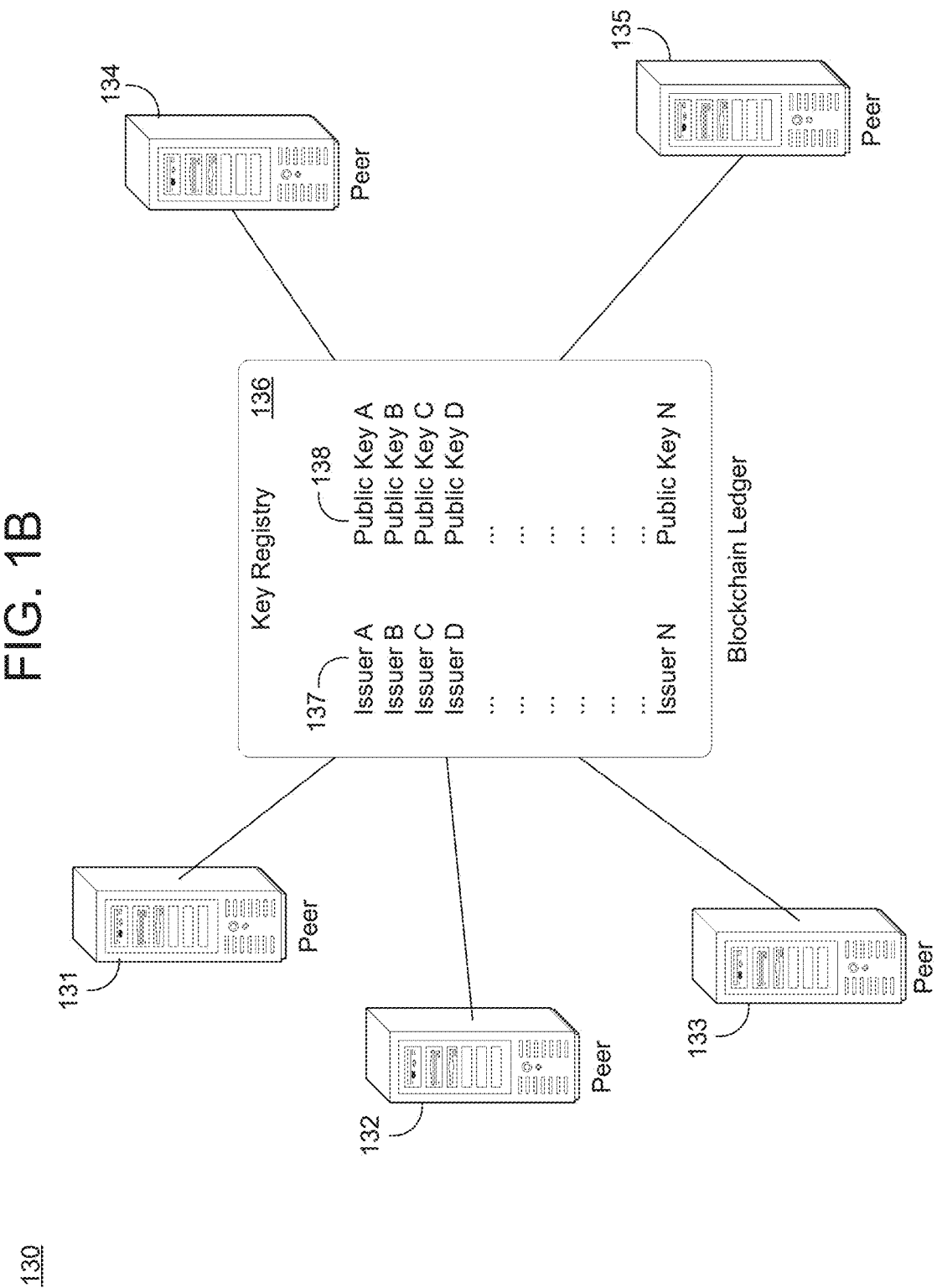

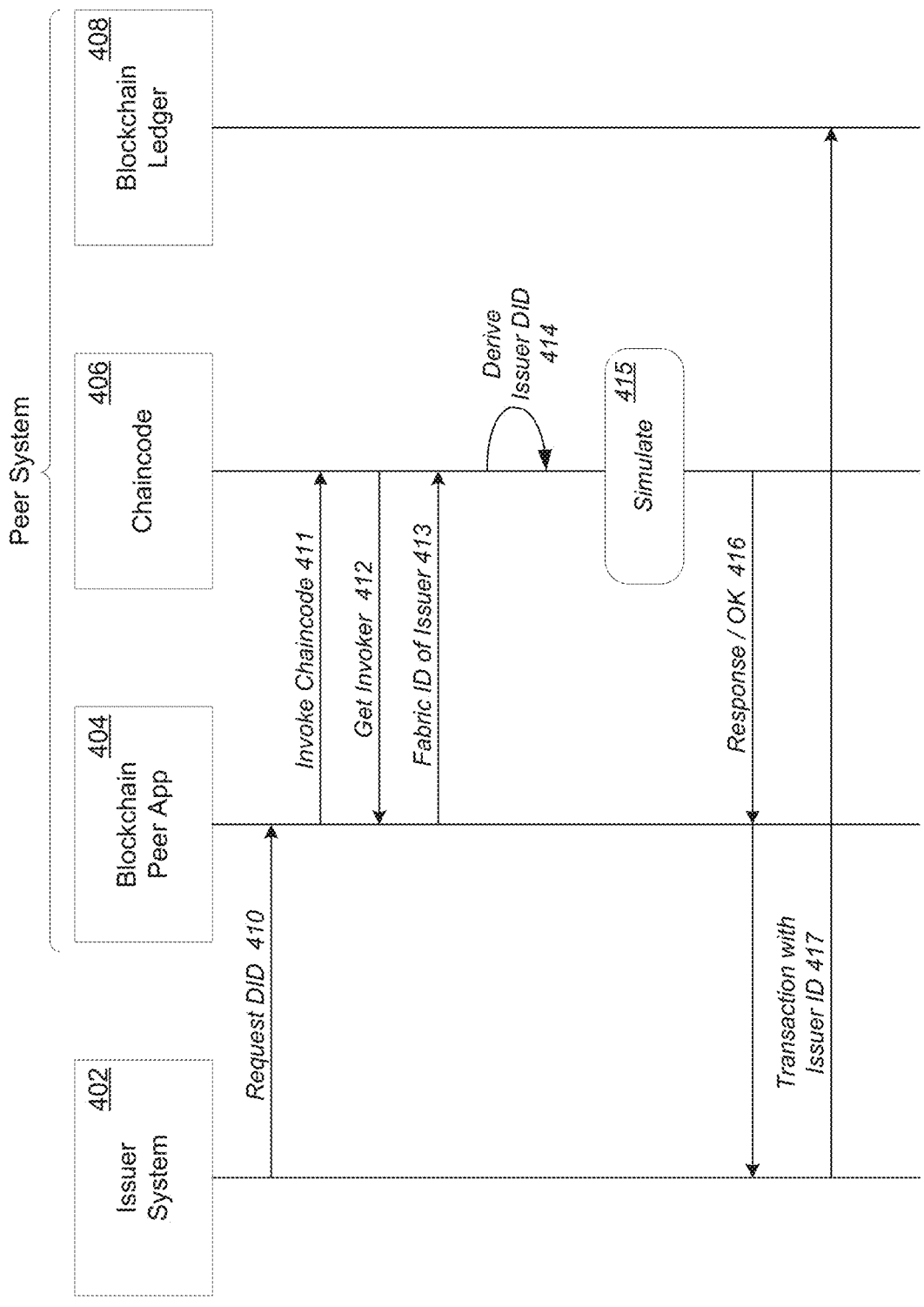

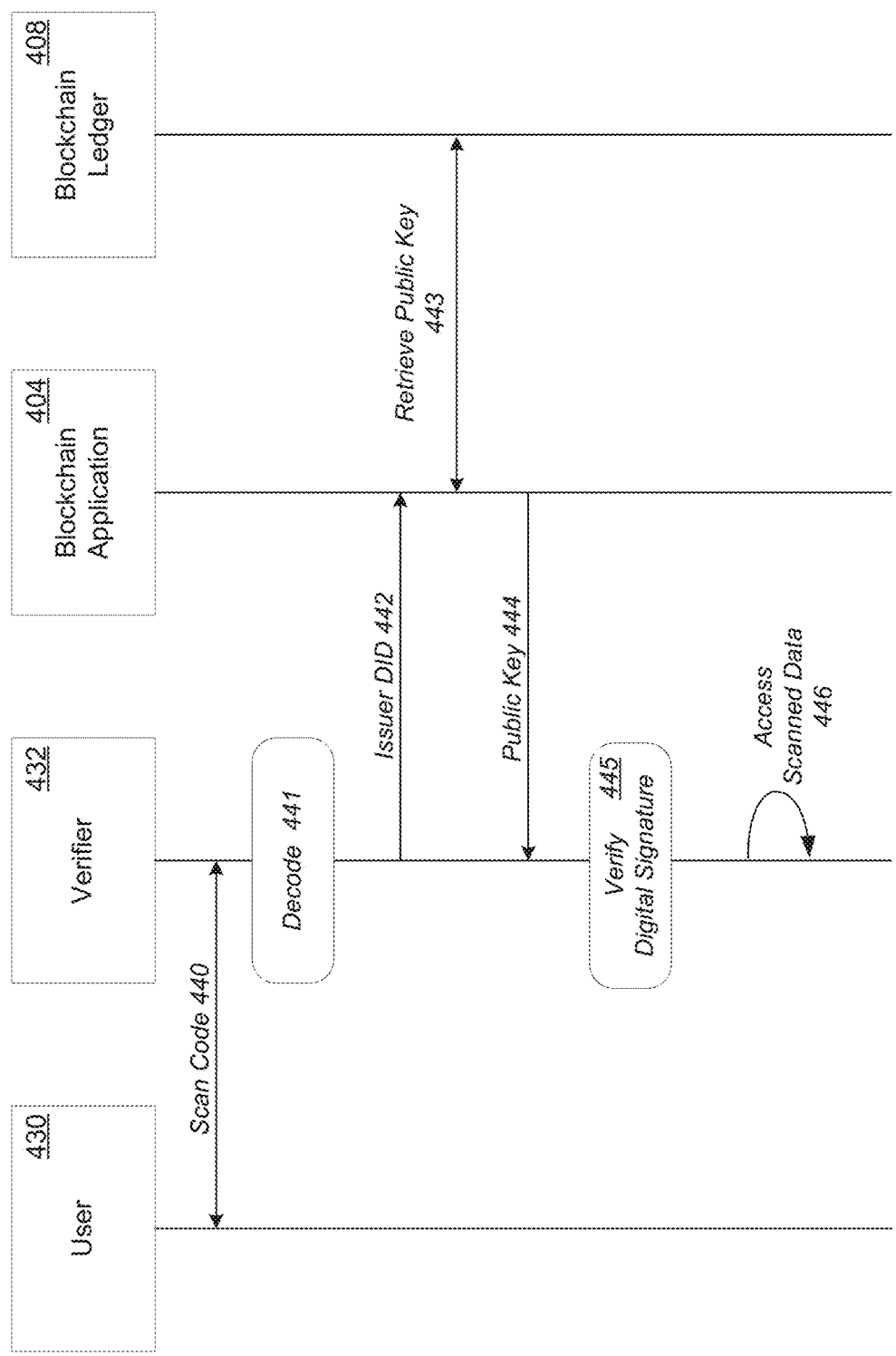

800
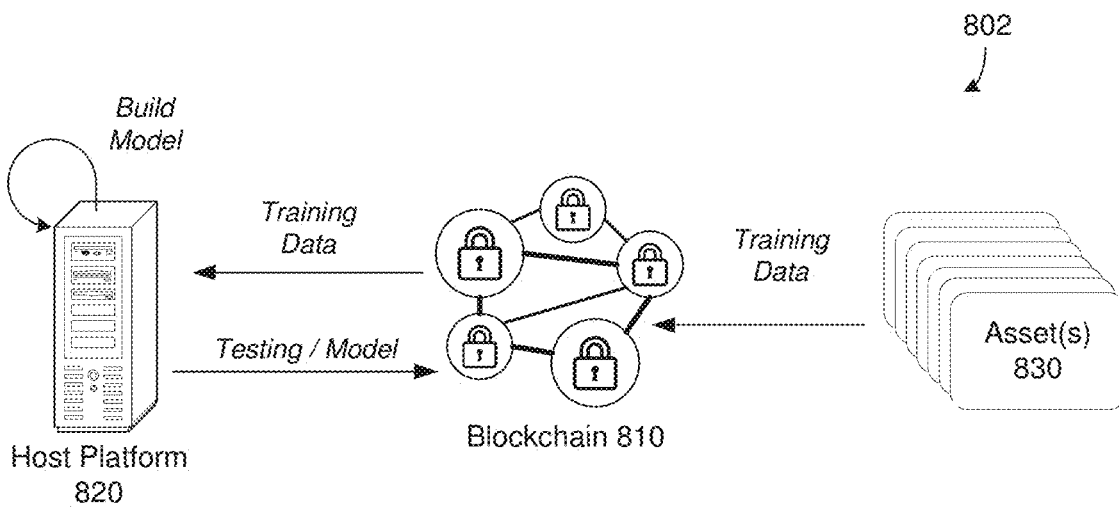
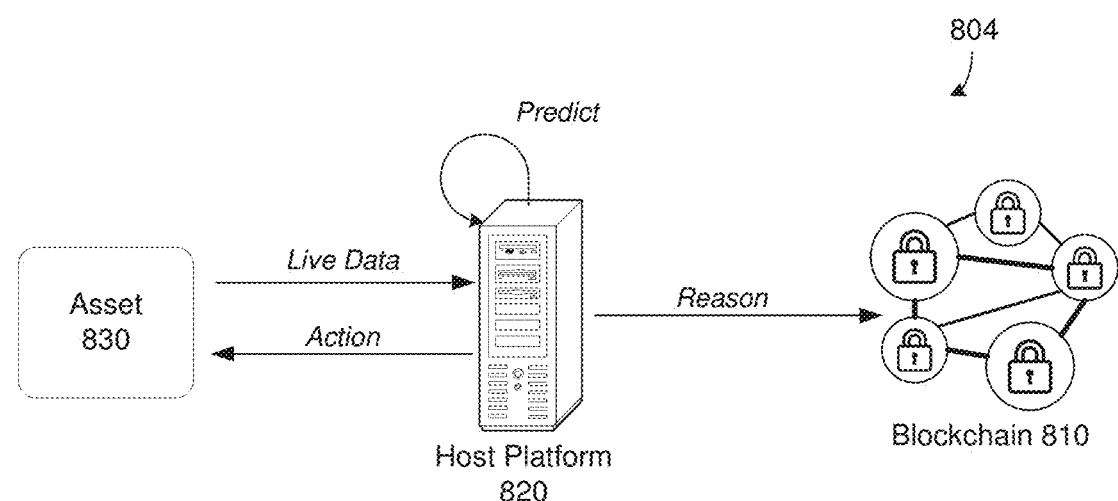
FIG. 8A

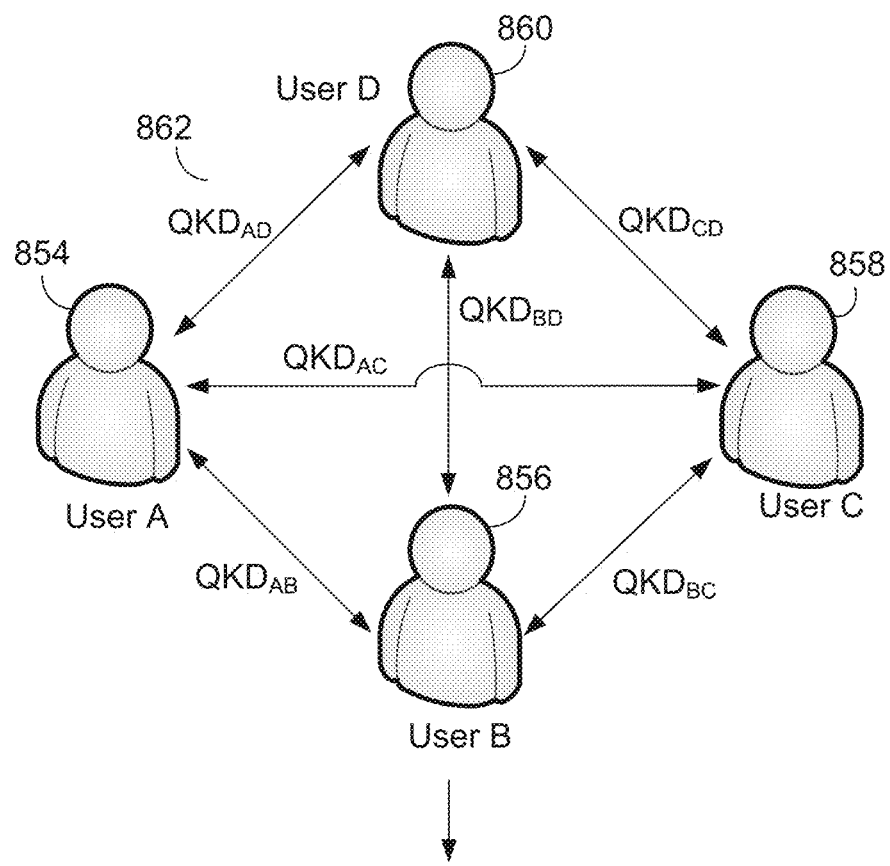
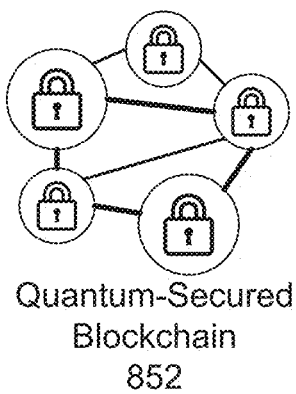
FIG. 8B

US 12,010,244 B2

BLOCKCHAIN BASED VERIFIABILITY OF USER STATUS

BACKGROUND

A centralized platform stores and maintains data in a single location. This location is often a central computer, for example, a cloud computing environment, a web server, a mainframe computer, or the like. Information stored on a centralized platform is typically accessible from multiple different points. Multiple users or client workstations can work simultaneously on the centralized platform, for example, based on a client/server configuration. A centralized platform is easy to manage, maintain, and control, especially for purposes of security because of its single location. Within a centralized platform, data redundancy is minimized as a single storing place of all data also implies that a given set of data only has one primary record.

SUMMARY

One example embodiment provides an apparatus that includes a processor that is configured to one or more of extract a data object from a machine-readable code, where the data object comprises fields of data signed with a digital signature of a private key, detect an identifier of an issuer of the data object from the extracted data object, retrieve a public key from a blockchain based on the identifier of the issuer detected from the field of the extracted data object, and verify the digital signature of the private key based on the fetched public key.

Another example embodiment provides a method that includes one or more of extracting a data object from a machine-readable code, where the data object comprises fields of data signed with a digital signature of a private key, detecting an identifier of an issuer of the data object from the extracted data object, retrieving a public key from a blockchain based on the identifier of the issuer detected from the field of the extracted data object, and verifying the digital signature of the private key based on the fetched public key.

A further example embodiment provides a non-transitory computer-readable medium comprising instructions, that when read by a processor, cause the processor to perform one or more of extracting a data object from a machine-readable code, where the data object comprises fields of data signed with a digital signature of a private key, detecting an identifier of an issuer of the data object from the extracted data object, retrieving a public key from a blockchain based on the identifier of the issuer detected from the field of the extracted data object, and verifying the digital signature of the private key based on the fetched public key.

BRIEF DESCRIPTION OF THE DRAWINGS

FIG. 1A is a diagram illustrating a certificate converted into a machine-readable code according to example embodiments.

FIG. 1B is a diagram illustrating a blockchain network managing a registry of identities and keys according to example embodiments.

FIG. 4A is a diagram illustrating a communication process of onboarding an issuer to the blockchain according to example embodiments.

FIG. 4B is a diagram illustrating a communication process for verifying a scanned certificate according to example embodiments.

FIG. 8A is a diagram illustrating an example blockchain which stores machine learning (artificial intelligence) data, according to example embodiments.

FIG. 8B is a diagram illustrating an example quantum-secure blockchain, according to example embodiments.

DETAILED DESCRIPTION

Figure 1C:
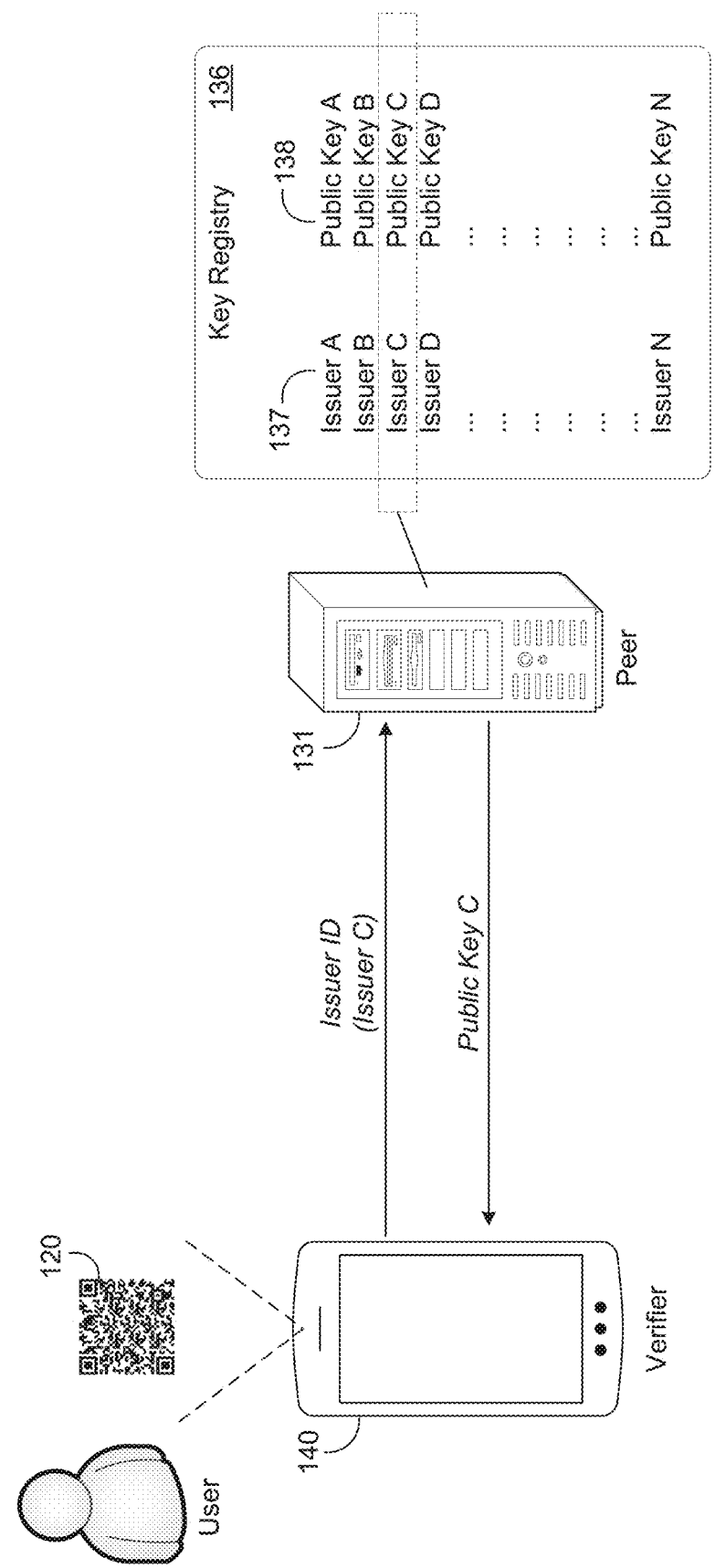
FIG. 1C is a diagram illustrating a process of verifying a scanned certificate according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

The instant features, structures, or characteristics as described throughout this specification may be combined or removed in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined or removed in any suitable manner in one or more embodiments. Further, in the diagrams, any connection between elements can permit one-way and/or two-way communication even if the depicted connection is a one-way or two-way arrow. Also, any device depicted in the drawings can be a different device. For example, if a mobile device is shown sending information, a wired device could also be used to send the information.

In addition, while the term "message" may have been used in the description of embodiments, the application may be applied to many types of networks and data. Furthermore, while certain types of connections, messages, and signaling may be depicted in exemplary embodiments, the application is not limited to a certain type of connection, message, and signaling.

Example embodiments provide methods, systems, components, non-transitory computer readable media, devices, and/or networks, which are directed to verifying the authenticity of a data certificate, for example, a health certificate, a document, an identification, or the like.

As described herein, the certificate may be a data object such as a document, a record, a digital file, a passport, and the like. The certificate may include one or more fields filled with one or more data values. As a non-limiting example, the certificate may certify the health of an individual, for example, whether the individual has tested negative for a particular virus, disease, or other ailment. The certificate may have a predefined schema which defines what data values/fields must be present, a type of the data (e.g., Boolean, string, Integer, array, etc.), how the data values are to be arranged, and the like. In addition to the data values, the user and the schema may be identified within fields of the certificate. To "issue" the certificate, an issuer (e.g., a doctor's office, a hospital, an employer, an agency, etc.) may sign the certificate using a private key of the issuer. The signing may create a hash of the content of the certificate which can be decrypted using a corresponding public key of the issuer. The issuer may also convert the signed certificate into a machine-readable code such as a quick response (QR) code, a bar code, or the like. Furthermore, the machine-readable code may be transmitted to an application on a user's device, printed to paper, or the like. Thus, a user who's data is stored in the certificate may carry around a machine-readable code that includes the signed certificate encoded therein.

The schema may be predefined by an issuer, a blockchain, an authority, or the like. The schema may be selected from among a plurality of schemas that are accessible to the issuer. For example, the different schemas may be stored in a registry on the blockchain ledger. The schema may define how data should be structured and what is required to be included and what is optional. Examples of schemas include schemas provided by YAML Ain't Markup Language (YAML), JavaScript Object Notation (JSON), and the like, which can describe any structure possible. The schema also identifies what specific pieces of data can be collapsed (e.g., represented by a hash, a digest, etc.), instead of including the entire data. In the example embodiments, the issuer may generate the certificate in a predefined schema and add an identifier of the schema to the certificate.

To use the signed certificate, the user may provide the machine-readable code to a verification entity (e.g., an employer, a stadium, an airline, an agency, etc.). For example, the verification entity may use a device (e.g., having an imaging element such as a camera, etc.) to scan the machine-readable code from the user's device, a piece of paper, or the like. The verifier's device may decode the machine-readable code to reveal the contents of the signed certificate. In addition to the data values, the contents may include an identifier of the user, an identifier of the issuer, test results, a timestamp, and the like. The verification entity may transmit the identifier of the issuer to the blockchain which stores a registry of keys. In response, the blockchain may look-up the corresponding public key of the issuer based on the identifier of the issuer and provide the verifier with the public key. Thus, the verification entity can verify the digital signature (made with the issuer's private key) based on the issuer's public key retrieved from the blockchain. Once verified, the verifier can trust the contents of the certificate.

The certificate can be used to certify personal data about a user (e.g., health-related data, work-related data, personal data, etc.) without storing such data or making such data accessible to others. In the example embodiments, the user data may only be encoded within the machine-readable code. That means that the user's data is not made accessible to anyone who is not in the physical presence of the machine-readable code, and who has access to the issuer's public key. Thus, the user's data can be securely provided to a verifier while also ensuring that the data being provided is authentic because of the issuer's digital signature with the private key.

In one embodiment this application utilizes a decentralized database (such as a blockchain) that is a distributed storage system, which includes multiple nodes that communicate with each other. The decentralized database includes an append-only immutable data structure resembling a distributed ledger capable of maintaining records between mutually untrusted parties. The untrusted parties are referred to herein as peers or peer nodes. Each peer maintains a copy of the database records and no single peer can modify the database records without a consensus being reached among the distributed peers. For example, the peers may execute a consensus protocol to validate blockchain storage transactions, group the storage transactions into blocks, and build a hash chain over the blocks. This process forms the ledger by ordering the storage transactions, as is necessary, for consistency. In various embodiments, a permissioned and/or a permissionless blockchain can be used. In a public or permission-less blockchain, anyone can participate without a specific identity. Public blockchains can involve native cryptocurrency and use consensus based on various protocols such as Proof of Work (PoW). On the other hand, a permissioned blockchain database provides secure interactions among a group of entities which share a common goal but which do not fully trust one another, such as businesses that exchange funds, goods, information, and the like.

This application can utilize a blockchain that operates arbitrary, programmable logic, tailored to a decentralized storage scheme and referred to as "smart contracts" or "chaincodes." In some cases, specialized chaincodes may exist for management functions and parameters which are referred to as system chaincode. The application can further utilize smart contracts that are trusted distributed applications which leverage tamper-proof properties of the blockchain database and an underlying agreement between nodes, which is referred to as an endorsement or endorsement policy. Blockchain transactions associated with this application can be "endorsed" before being committed to the blockchain while transactions, which are not endorsed, are disregarded. An endorsement policy allows chaincode to specify endorsers for a transaction in the form of a set of peer nodes that are necessary for endorsement. When a client sends the transaction to the peers specified in the endorsement policy, the transaction is executed to validate the transaction. After validation, the transactions enter an ordering phase in which a consensus protocol is used to produce an ordered sequence of endorsed transactions grouped into blocks.

This application can utilize nodes that are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node which submits a transaction-invocation to an endorser (e.g., peer), and broadcasts transaction-proposals to an ordering service (e.g., ordering node). Another type of node is a peer node which can receive client submitted transactions, commit the transactions and maintain a state and a copy of the ledger of blockchain transactions. Peers can also have the role of an endorser, although it is not a requirement. An ordering-service-node or orderer is a node running the communication service for all nodes, and which implements a delivery guarantee, such as a broadcast to each of the peer nodes in the system when committing transactions and modifying a world state of the blockchain, which is another name for the initial blockchain transaction which normally includes control and setup information.

This application can utilize a ledger that is a sequenced, tamper-resistant record of all state transitions of a blockchain. State transitions may result from chaincode invocations (i.e., transactions) submitted by participating parties (e.g., client nodes, ordering nodes, endorser nodes, peer nodes, etc.). Each participating party (such as a peer node) can maintain a copy of the ledger. A transaction may result in a set of asset key-value pairs being committed to the ledger as one or more operands, such as creates, updates, deletes, and the like. The ledger includes a blockchain (also referred to as a chain) which is used to store an immutable, sequenced record in blocks. The ledger also includes a state database which maintains a current state of the blockchain.

This application can utilize a chain that is a transaction log which is structured as hash-linked blocks, and each block contains a sequence of N transactions where N is equal to or greater than one. The block header includes a hash of the block's transactions, as well as a hash of the prior block's header. In this way, all transactions on the ledger may be sequenced and cryptographically linked together. Accordingly, it is not possible to tamper with the ledger data without breaking the hash links. A hash of a most recently added blockchain block represents every transaction on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain transaction log. Since the current state represents the latest key values known to a channel, it is sometimes referred to as a world state. Chaincode invocations execute transactions against the current state data of the ledger. To make these chaincode interactions efficient, the latest values of the keys may be stored in a state database. The state database may be simply an indexed view into the chain's transaction log, it can therefore be regenerated from the chain at any time. The state database may automatically be recovered (or generated if needed) upon peer node startup, and before transactions are accepted.

Some of the benefits provided by the example embodiments include the ability of a user to provide personal information certified by a third-party via a blockchain, without such personal information being stored on the blockchain. Blockchain makes the certificate management process decentralized, more transparent, and robust against unauthorized modifications, which is very important to gain trust. Furthermore, the blockchain is amenable to interoperability across different jurisdictions. For example, the certificate could be used on an international level. Blockchain enables different jurisdictions, with different rules and regulations, to transact together in a decentralized, trusted, and secure manner through the blockchain.

While it is easy for a person to show a paper certificate from a lab testing facility to a verify the health of the person, such paper certificates are easily subject to counterfeiting. For example, a verifier receiving the paper certificate does not have means to validate the paper certificate. As a result, the verifier must contact the issuer of the certificate (e.g., a lab testing facility, doctor's office, hospital, etc.).

The example embodiments overcome these drawback through the use of a blockchain to support decentralized secure verification of the contents of a certificate. The blockchain ensures unforgeability of claims (certificates), non-transferability of a certificate from one user to another, non-repudiation of issued certificates by their issuers, privacy because no personally identifiable information (PII) of the user red on the blockchain, and scalability because the blockchain network can add many issuers and verifiers, enabling many users to have certificates verified. The blockchain also enables compatibility with standards, namely W3C standards on decentralized identities (DIDs) and verifiable credentials (VCs).

FIG. 1A illustrates a certificate 110 that is converted into a machine-readable code 120 according to example embodiments. Referring to FIG. 1A, the certificate 110 in this example includes a health-related certificate that provides information about a health checkup (e.g., a test for a virus) that has been performed on a user. In this example, the certificate 110 includes a plurality of fields 112 and a plurality of values 114 stored in the fields. In some embodiments, the fields 112 may have string-based identifiers that recite the name of the field, however, embodiments are not limited thereto. The values may be string, numeral, Boolean, arrays, or the like. In addition, one or more digital signatures 116 of an issuer that issued the certificate 110 may be included within the certificate 110.

The data fields in the certificate 110 of FIG. 1A include a unique identifier which uniquely identifies the certificate 110 on the blockchain, a schema identifier which identifies the schema required by the certificate 110, a user identifier which identifiers the person who is associated with the data within the certificate 110, an issuer ID which identifies the signer of the digital signature 116, and a lab ID. The certificate 110 may also include an identifier of the test performed on the user, a timestamp, a test type performed, a result (pass/fail), another digital signature, and the like. It should be appreciated that while the example of FIG. 1A is directed to a health-related certificate, the data content within the certificate is not limited to just use with health data. Other types of data include, but are not limited to, employment data, identification documents, certificates of merit, tickets, coupons, and the like.

An issuer of the certificate 110 may use a computing device to convert the certificate 110 into the machine-readable code 120 such as a QR code. For example, the computing device may have a QR code generator application that is executing thereon. The QR code is a two-dimensional barcode. It encodes alphanumeric information. To decode the QR code, a user can capture an image of the QR code with a handheld QR scanner or camera on a smartphone (with a QR decoding application thereon) which decodes the QR code to reveal the underlying content of the certificate 110. For example, the result of the decoding may be a single string with the fields/values of the certificate therein concatenated together. The resulting QR code 120 may be printed to paper, transmitted to a mobile application on a user device, or the like. Thus, a user can carry around the QR code 120 to prove that the user has passed a particular health-related test, or the like.

FIG. 1B illustrates a blockchain network 130 for managing a registry 136 of identities 137 and keys 138 according to example embodiments. Referring to FIG. 1B, the blockchain network 130 may be a permissioned blockchain network which includes a plurality of blockchain peers 131-135. Each blockchain peer 131-135 may store a copy of a blockchain ledger which implements a registry 136 for storing keys of issuers of certificates 110. The registry may include a list of issuers 137 and corresponding public keys 138. For example, each time a new issuer registers (initially) with the blockchain network 130, a blockchain transaction may be submitted which records an identifier of the issuer 137 and a public key 138 of the issuer 137.

Although not shown in FIG. 1B, the blockchain ledger may maintain a blockchain (chain of blocks storing transaction content) and a state database (e.g., a world state database) which stores key value pairs of keys from the blockchain. For example, a key may be an identifier of an issuer and a corresponding value may be a corresponding public key of that issuer. Meanwhile, the blockchain may be used to store the transaction content including the issuer identifiers and public keys as they are stored on the blockchain. As new issuers are added to the system, the registry 136 may be updated to add new issuers and new keys. Likewise, as existing issuers are removed from the system, the registry 136 may be updated to delete the issuers and the corresponding public keys.

The blockchain network 130 may also store and manage schemas that can be used by issuers to create certificates. Each schema may be identified by a schema identifier and stored on the blockchain. The schema may specify how application-specific data should be parsed into a list of fields that must be included in the certificate, data types of the fields (e.g., string, array, integer, Boolean, etc.), an identification of which fields may be hashed and which fields may not be hashed, and the like. The schema identifier of a particular certificate may be encoded within the machine-readable code 120 and identified by a verifier (e.g., verifier 140 shown in FIG. 1C) when the machine-readable code is scanned.

The schema provides an additional layer of security and authenticity to the certificate. The digital signature signed by the issuer may be a signature over some application-specific data that is parsed according to a specified schema. The solution guarantees that it's impossible to interpret a credential encoded according to schema A as if it had been encoded using schema B (schema confusion), and II) schema definitions are stored in the blockchain and so also enjoy the properties of integrity and consensus as general ledger data.

The example embodiments also permit selective disclosure of fields in the certificate. For example, if a certificate has two fields, only one of the fields may be disclosed while the other field is not. In this case, each field may have a field identifier and a value (sensitive data). In order to disclose the value of the field two but not the value in field one, the issuer may hash the first field prior to signing the first field. In doing so, the verified may verify that the hash of the first field hasn't changed, but not be able to detect the underlying value of the first field because the verifier will not have access to the hash function.

When an issuer generates a certificate which is encoded and given to a user, the issuer may sign the content of the certificate with their private key. The digital signature may create a hash over the content. FIG. 1C illustrates a process 100C of verifying a certificate that is decoded from the machine-readable code 120, according to example embodiments. According to various embodiments, the issuer can include their unique identifier within the machine-readable code 120 when encoding the certificate. For example, the issuer may include a field within the encoded machine-readable code that can be read and decoded by a QR code scanning application, etc.

Referring to FIG. 1C, a user can present the machine-readable code 120 via a piece of paper, via an application on a mobile device, and the like. The verifier 140 can read the machine-readable code 120 with an imaging device such as a camera, scanner, etc., decode the machine-readable code 120, and identify an issuer from a field of the decoded machine-readable code. In this example, the verifier identifies issuer C. The verifier 140 can use this information to retrieve the corresponding public key of the issuer from the registry 136 managed by the blockchain network 130. For example, the verifier 140 may transmit a request to a blockchain peer 131 along with an identifier of the issuer decoded from the machine-readable code 120. The blockchain peer 131 may access the key registry 136 on the blockchain ledger, retrieve the corresponding public key (i.e., issuer C's public key) and transmit the public key to the verifier 140.

As an example, the digital signature added to the certificate may be a hash of the certificate content that is subsequently encrypted with the issuer's private key. To verify the digital signature, the verifier 140 may decrypt the digital signature using the retrieved public key to obtain the original hash content created by the issuer. The verifier 140 may also perform a same hash on the certificate data as was performed by the issuer. The verifier 140 may then compare the two hash values. If the two hash values are the same, the digital signature is verified.

To facilitate communication between the user, the blockchain network, and the verifier, the verifier may implement a number of application programming interfaces (APIs). For example, a the verifier may run a software application (e.g., a mobile application) that provides an API for scanning and decoding the QR code with the certificate data encoded therein, an API for determining an issuer identifier from the scanned QR code, an API for getting the schema of the credential from the scanned QR code, an API for requesting the public key of the issuer from the blockchain network, and the like.

Figure 2A:
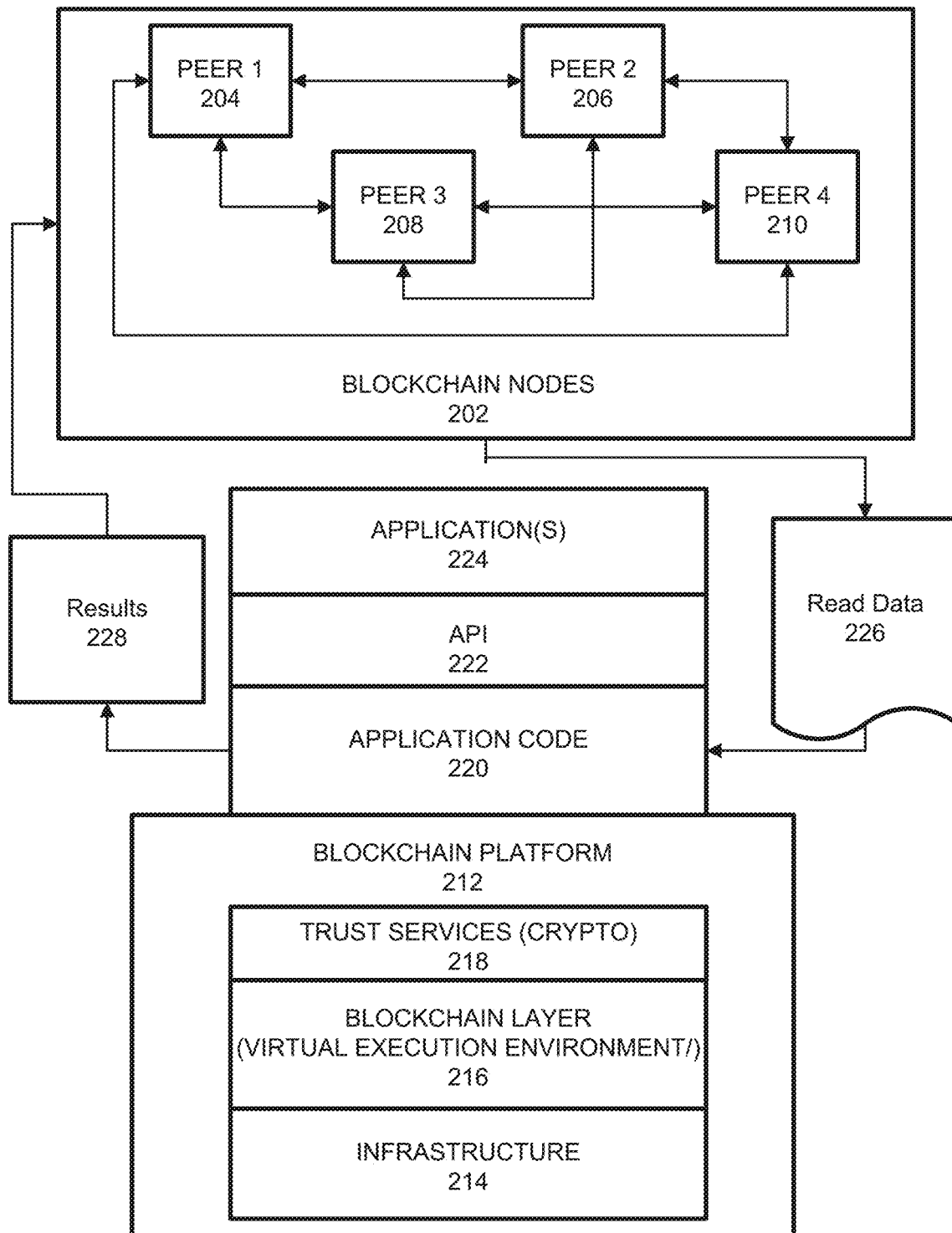
FIG. 2A is a diagram illustrating an example blockchain architecture configuration, according to example embodiments.

FIG. 2A illustrates a blockchain architecture configuration 200, according to example embodiments. Referring to FIG. 2A, the blockchain architecture 200 may include certain blockchain elements, for example, a group of blockchain nodes 202. The blockchain nodes 202 may include one or more nodes 204-210 (these four nodes are depicted by example only). These nodes participate in a number of activities, such as blockchain transaction addition and validation process (consensus). One or more of the blockchain nodes 204-210 may endorse transactions based on endorsement policy and may provide an ordering service for all blockchain nodes in the architecture 200. A blockchain node may initiate a blockchain authentication and seek to write to a blockchain immutable ledger stored in blockchain layer 216, a copy of which may also be stored on the underpinning physical infrastructure 214. The blockchain configuration may include one or more applications 224 which are linked to application programming interfaces (APIs) 222 to access and execute stored program/application code 220 (e.g., chaincode, smart contracts, etc.) which can be created according to a customized configuration sought by participants and can maintain their own state, control their own assets, and receive external information. This can be deployed as a transaction and installed, via appending to the distributed ledger, on all blockchain nodes 204-210.

The blockchain base or platform 212 may include various layers of blockchain data, services (e.g., cryptographic trust services, virtual execution environment, etc.), and underpinning physical computer infrastructure that may be used to receive and store new transactions and provide access to auditors which are seeking to access data entries. The blockchain layer 216 may expose an interface that provides access to the virtual execution environment necessary to process the program code and engage the physical infrastructure 214. Cryptographic trust services 218 may be used to verify transactions such as asset exchange transactions and keep information private.

The blockchain architecture configuration of FIG. 2A may process and execute program/application code 220 via one or more interfaces exposed, and services provided, by blockchain platform 212. The code 220 may control blockchain assets. For example, the code 220 can store and transfer data, and may be executed by nodes 204-210 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements and usage of the ledger. For example, the smart contract (or chaincode executing the logic of the smart contract) may read blockchain data 226 which may be processed by one or more processing entities (e.g., virtual machines) included in the blockchain layer 216 to generate results 228 including alerts, determining liability, and the like, within a complex service scenario. The physical infrastructure 214 may be utilized to retrieve any of the data or information described herein.

A smart contract may be created via a high-level application and programming language, and then written to a block in the blockchain. The smart contract may include executable code which is registered, stored, and/or replicated with a blockchain (e.g., distributed network of blockchain peers). A transaction is an execution of the smart contract logic which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into one or more blocks within the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A chaincode may include the code interpretation (e.g., the logic) of a smart contract. For example, the chaincode may include a packaged and deployable version of the logic within the smart contract. As described herein, the chaincode may be program code deployed on a computing network, where it is executed and validated by chain validators together during a consensus process. The chaincode may receive a hash and retrieve from the blockchain a hash associated with the data template created by use of a previously stored feature extractor. If the hashes of the hash identifier and the hash created from the stored identifier template data match, then the chaincode sends an authorization key to the requested service. The chaincode may write to the blockchain data associated with the cryptographic details.

Figure 2B:
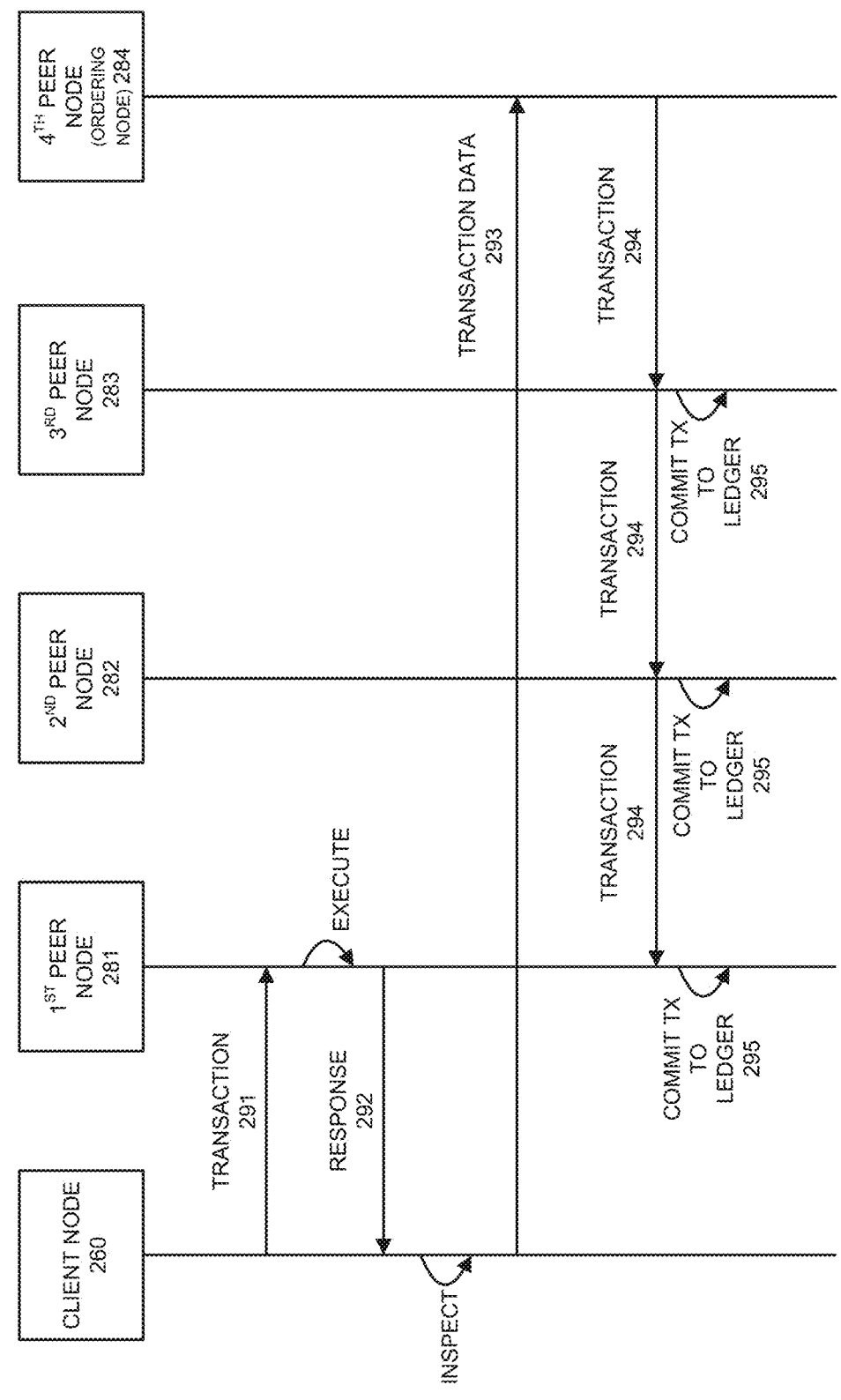
FIG. 2B is a diagram illustrating a blockchain transactional flow among nodes, according to example embodiments.

FIG. 2B illustrates an example of a blockchain transactional flow 250 between nodes of the blockchain in accordance with an example embodiment. Referring to FIG. 2B, the transaction flow may include a client node 260 transmitting a transaction proposal 291 to an endorsing peer node 281. The endorsing peer 281 may verify the client signature and execute a chaincode function to initiate the transaction. The output may include the chaincode results, a set of key/value versions that were read in the chaincode (read set), and the set of keys/values that were written in chaincode (write set). Here, the endorsing peer 281 may determine whether or not to endorse the transaction proposal. The proposal response 292 is sent back to the client 260 along with an endorsement signature, if approved. The client 260 assembles the endorsements into a transaction payload 293 and broadcasts it to an ordering service node 284. The ordering service node 284 then delivers ordered transactions as blocks to all peers 281-283 on a channel. Before committal to the blockchain, each peer 281-283 may validate the transaction. For example, the peers may check the endorsement policy to ensure that the correct allotment of the specified peers have signed the results and authenticated the signatures against the transaction payload 293.

Referring again to FIG. 2B, the client node initiates the transaction 291 by constructing and sending a request to the peer node 281, which is an endorser. The client 260 may include an application leveraging a supported software development kit (SDK), which utilizes an available API to generate a transaction proposal. The proposal is a request to invoke a chaincode function so that data can be read and/or written to the ledger (i.e., write new key value pairs for the assets). The SDK may serve as a shim to package the transaction proposal into a properly architected format (e.g., protocol buffer over a remote procedure call (RPC)) and take the client's cryptographic credentials to produce a unique signature for the transaction proposal.

In response, the endorsing peer node 281 may verify (a) that the transaction proposal is well formed, (b) the transaction has not been submitted already in the past (replay-attack protection), (c) the signature is valid, and (d) that the submitter (client 260, in the example) is properly authorized to perform the proposed operation on that channel. The endorsing peer node 281 may take the transaction proposal inputs as arguments to the invoked chaincode function. The chaincode is then executed against a current state database to produce transaction results including a response value, read set, and write set. However, no updates are made to the ledger at this point. In 292, the set of values, along with the endorsing peer node's 281 signature is passed back as a proposal response 292 to the SDK of the client 260 which parses the payload for the application to consume.

In response, the application of the client 260 inspects/verifies the signatures of the endorsing peers and compares the proposal responses to determine if the proposal response is the same. If the chaincode only queried the ledger, the application would inspect the query response and would typically not submit the transaction to the ordering node service 284. If the client application intends to submit the transaction to the ordering node service 284 to update the ledger, the application determines if the specified endorsement policy has been fulfilled before submitting (i.e., did all peer nodes necessary for the transaction endorse the transaction). Here, the client may include only one of multiple parties to the transaction. In this case, each client may have their own endorsing node, and each endorsing node will need to endorse the transaction. The architecture is such that even if an application selects not to inspect responses or otherwise forwards an unendorsed transaction, the endorsement policy will still be enforced by peers and upheld at the commit validation phase.

After successful inspection, in step 293 the client 260 assembles endorsements into a transaction proposal and broadcasts the transaction proposal and response within a transaction message to the ordering node 284. The transaction may contain the read/write sets, the endorsing peer signatures and a channel ID. The ordering node 284 does not need to inspect the entire content of a transaction in order to perform its operation, instead the ordering node 284 may simply receive transactions from all channels in the network, order them chronologically by channel, and create blocks of transactions per channel.

The blocks are delivered from the ordering node 284 to all peer nodes 281-283 on the channel. The data section within the block may be validated to ensure an endorsement policy is fulfilled and to ensure that there have been no changes to ledger state for read set variables since the read set was generated by the transaction execution. Furthermore, in step 295 each peer node 281-283 appends the block to the channel's chain, and for each valid transaction the write sets are committed to current state database. An event may be emitted, to notify the client application that the transaction (invocation) has been immutably appended to the chain, as well as to notify whether the transaction was validated or invalidated.

Figure 3A:
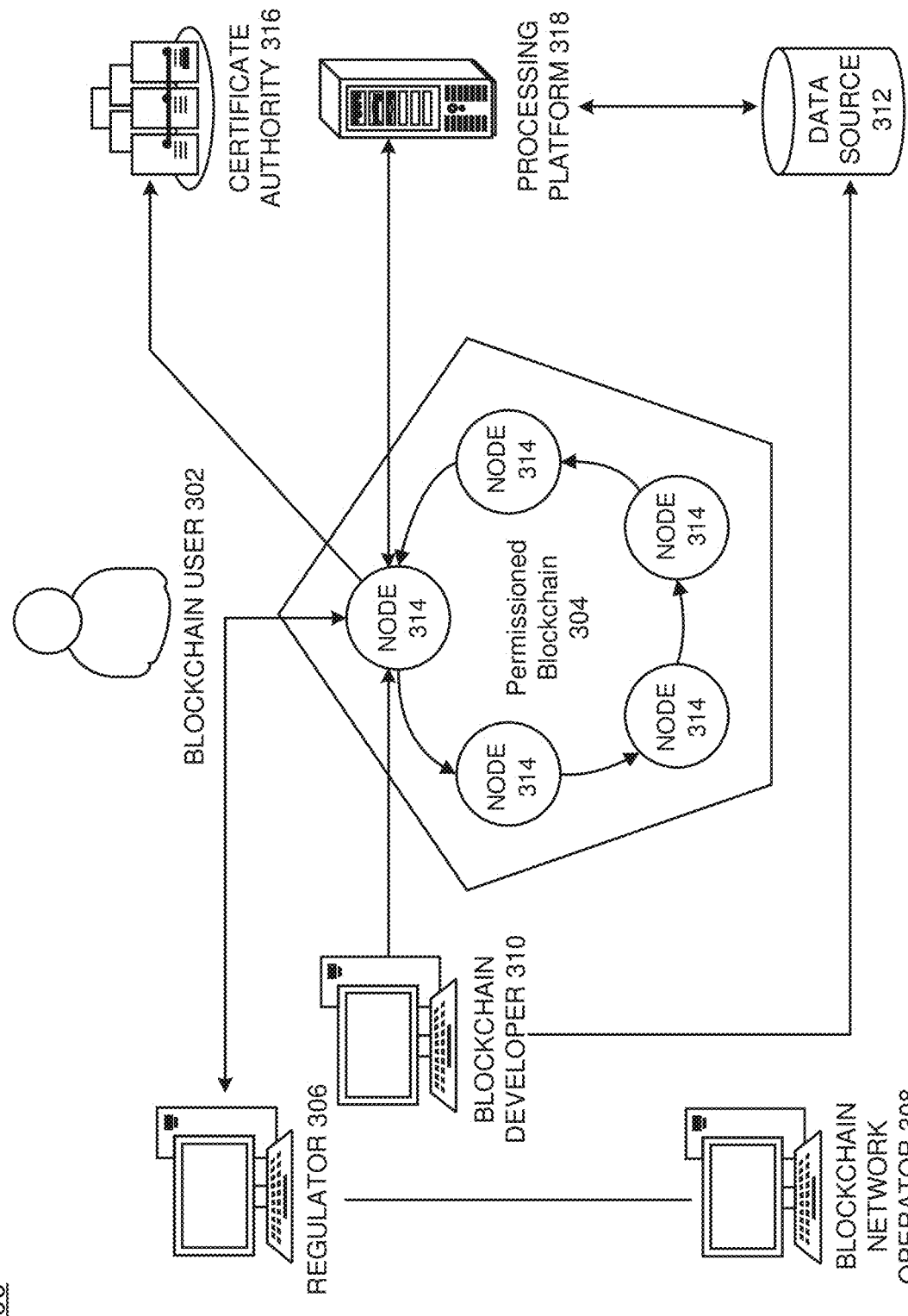
FIG. 3A is a diagram illustrating a permissioned network, according to example embodiments.

FIG. 3A illustrates an example of a permissioned blockchain network 300, which features a distributed, decentralized peer-to-peer architecture. In this example, a blockchain user 302 may initiate a transaction to the permissioned blockchain 304. In this example, the transaction can be a deploy, invoke, or query, and may be issued through a client-side application leveraging an SDK, directly through an API, etc. Networks may provide access to a regulator 306, such as an auditor. A blockchain network operator 308 manages member permissions, such as enrolling the regulator 306 as an "auditor" and the blockchain user 302 as a "client". An auditor could be restricted only to querying the ledger whereas a client could be authorized to deploy, invoke, and query certain types of chaincode.

A blockchain developer 310 can write chaincode and client-side applications. The blockchain developer 310 can deploy chaincode directly to the network through an interface. To include credentials from a traditional data source 312 in chaincode, the developer 310 could use an out-of-band connection to access the data. In this example, the blockchain user 302 connects to the permissioned blockchain 304 through a peer node 314. Before proceeding with any transactions, the peer node 314 retrieves the user's enrollment and transaction certificates from a certificate authority 316, which manages user roles and permissions. In some cases, blockchain users must possess these digital certificates in order to transact on the permissioned blockchain 304. Meanwhile, a user attempting to utilize chaincode may be required to verify their credentials on the traditional data source 312. To confirm the user's authorization, chaincode can use an out-of-band connection to this data through a traditional processing platform 318.

Figure 3B:
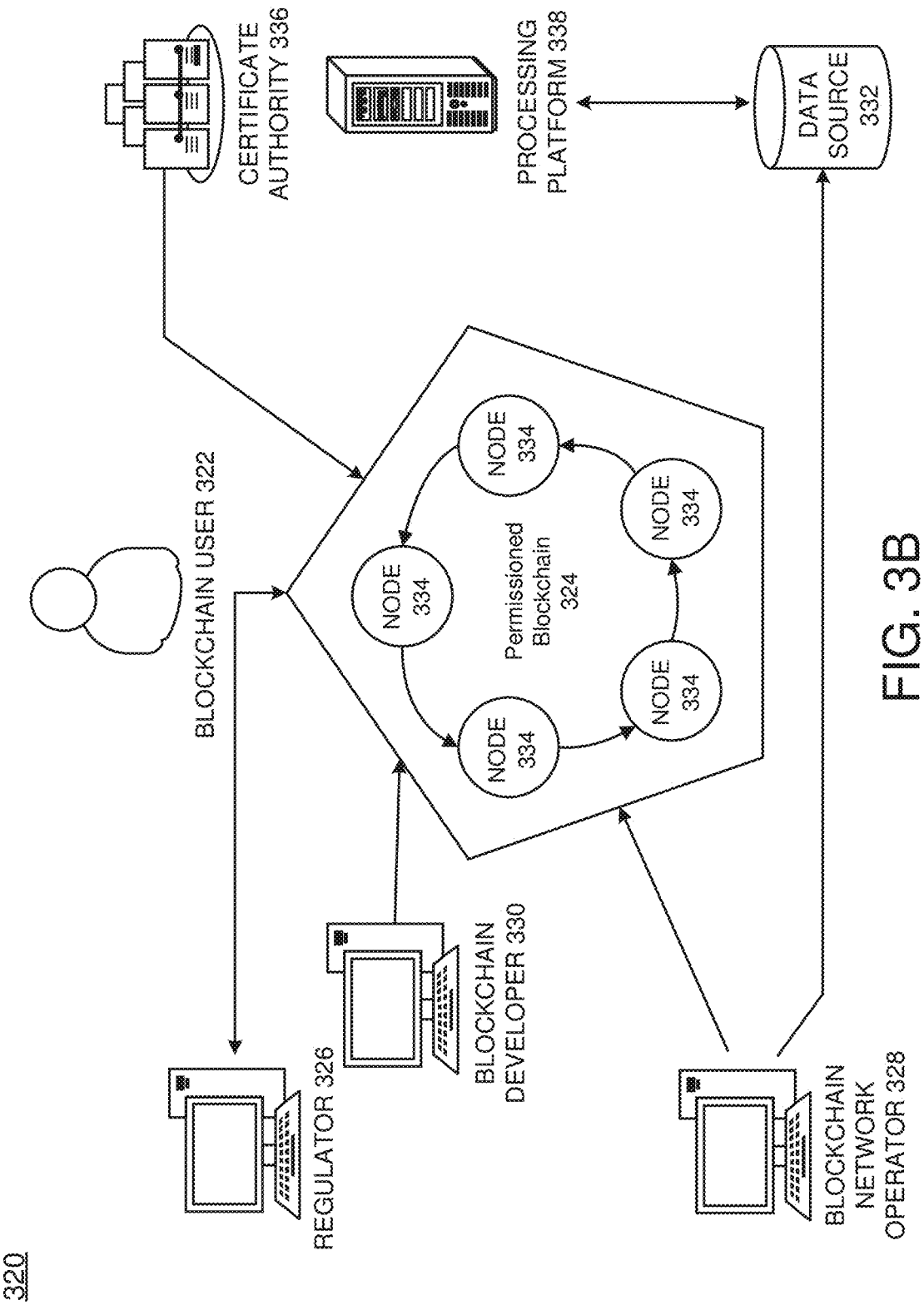
FIG. 3B is a diagram illustrating another permissioned network, according to example embodiments.

FIG. 3B illustrates another example of a permissioned blockchain network 320, which features a distributed, decentralized peer-to-peer architecture. In this example, a blockchain user 322 may submit a transaction to the permissioned blockchain 324. In this example, the transaction can be a deploy, invoke, or query, and may be issued through a client-side application leveraging an SDK, directly through an API, etc. Networks may provide access to a regulator 326, such as an auditor. A blockchain network operator 328 manages member permissions, such as enrolling the regulator 326 as an "auditor" and the blockchain user 322 as a "client". An auditor could be restricted only to querying the ledger whereas a client could be authorized to deploy, invoke, and query certain types of chaincode.

A blockchain developer 330 writes chaincode and client-side applications. The blockchain developer 330 can deploy chaincode directly to the network through an interface. To include credentials from a traditional data source 332 in chaincode, the developer 330 could use an out-of-band connection to access the data. In this example, the blockchain user 322 connects to the network through a peer node 334. Before proceeding with any transactions, the peer node 334 retrieves the user's enrollment and transaction certificates from the certificate authority 336. In some cases, blockchain users must possess these digital certificates in order to transact on the permissioned blockchain 324. Meanwhile, a user attempting to utilize chaincode may be required to verify their credentials on the traditional data source 332. To confirm the user's authorization, chaincode can use an out-of-band connection to this data through a traditional processing platform 338.

In some embodiments, the blockchain herein may be a permissionless blockchain. In contrast with permissioned blockchains which require permission to join, anyone can join a permissionless blockchain. For example, to join a permissionless blockchain a user may create a personal address and begin interacting with the network, by submitting transactions, and hence adding entries to the ledger. Additionally, all parties have the choice of running a node on the system and employing the mining protocols to help verify transactions.

Figure 3C:
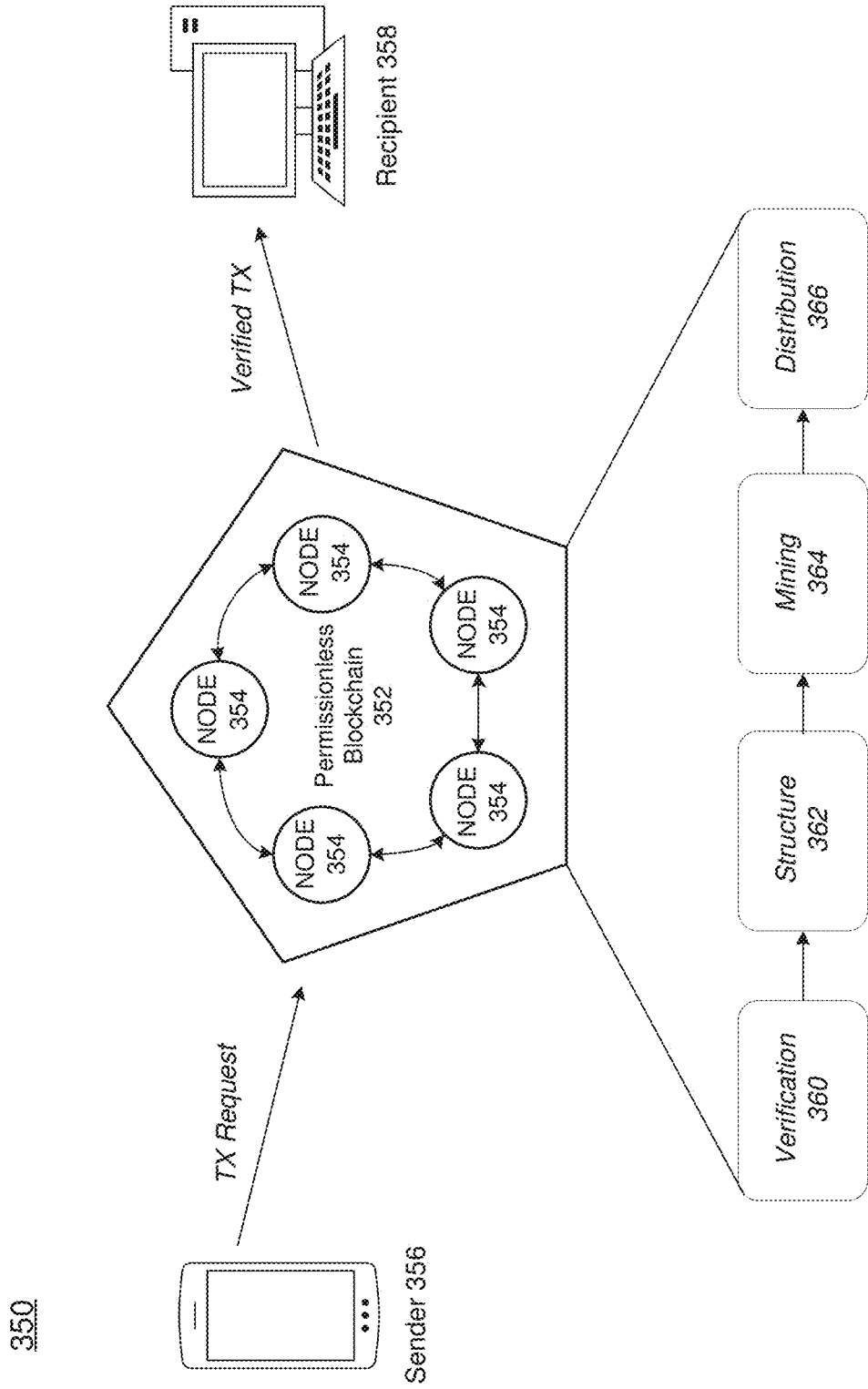
FIG. 3C is a diagram illustrating a permissionless network, according to example embodiments.

FIG. 3C illustrates a process 350 of a transaction being processed by a permissionless blockchain 352 including a plurality of nodes 354. A sender 356 desires to send payment or some other form of value (e.g., a deed, medical records, a contract, a good, a service, or any other asset that can be encapsulated in a digital record) to a recipient 358 via the permissionless blockchain 352. In one embodiment, each of the sender device 356 and the recipient device 358 may have digital wallets (associated with the blockchain 352) that provide user interface controls and a display of transaction parameters. In response, the transaction is broadcast throughout the blockchain 352 to the nodes 354. Depending on the blockchain's 352 network parameters the nodes verify 360 the transaction based on rules (which may be pre-defined or dynamically allocated) established by the permissionless blockchain 352 creators. For example, this may include verifying identities of the parties involved, etc. The transaction may be verified immediately or it may be placed in a queue with other transactions and the nodes 354 determine if the transactions are valid based on a set of network rules.

In structure 362, valid transactions are formed into a block and sealed with a lock (hash). This process may be performed by mining nodes among the nodes 354. Mining nodes may utilize additional software specifically for mining and creating blocks for the permissionless blockchain 352. Each block may be identified by a hash (e.g., 256 bit number, etc.) created using an algorithm agreed upon by the network. Each block may include a header, a pointer or reference to a hash of a previous block's header in the chain, and a group of valid transactions. The reference to the previous block's hash is associated with the creation of the secure independent chain of blocks.

Before blocks can be added to the blockchain, the blocks must be validated. Validation for the permissionless blockchain 352 may include a proof-of-work (PoW) which is a solution to a puzzle derived from the block's header. Although not shown in the example of FIG. 3C, another process for validating a block is proof-of-stake. Unlike the proof-of-work, where the algorithm rewards miners who solve mathematical problems, with the proof of stake, a creator of a new block is chosen in a deterministic way, depending on its wealth, also defined as "stake." Then, a similar proof is performed by the selected/chosen node.

With mining 364, nodes try to solve the block by making incremental changes to one variable until the solution satisfies a network-wide target. This creates the PoW thereby ensuring correct answers. In other words, a potential solution must prove that computing resources were drained in solving the problem. In some types of permissionless blockchains, miners may be rewarded with value (e.g., coins, etc.) for correctly mining a block.

Here, the PoW process, alongside the chaining of blocks, makes modifications of the blockchain extremely difficult, as an attacker must modify all subsequent blocks in order for the modifications of one block to be accepted. Furthermore, as new blocks are mined, the difficulty of modifying a block increases, and the number of subsequent blocks increases. With distribution 366, the successfully validated block is distributed through the permissionless blockchain 352 and all nodes 354 add the block to a majority chain which is the permissionless blockchain's 352 auditable ledger. Furthermore, the value in the transaction submitted by the sender 356 is deposited or otherwise transferred to the digital wallet of the recipient device 358.

FIG. 4A illustrates a communication process 400A of onboarding an issuer to the blockchain according to example embodiments. Referring to FIG. 4A, an issuer 402 registers with a blockchain network via a blockchain peer which includes a blockchain application 404, chaincode 406 (i.e., smart contract logic), and a blockchain ledger 408 (i.e., chain of blocks and a state database, etc.). Each blockchain peer in the blockchain network may include the blockchain application 4040, the chaincode 406, and the blockchain ledger 408.

In 410, the issuer 402 may request a unique identifier from the blockchain application 404. In response, the blockchain application 404 may invoke the chaincode 406 of the blockchain peer, in 411. The blockchain application 404 may receive an invoker from the chaincode 406, in 412, and request, from the chaincode 406, a unique identifier (DID) for use by the issuer 402 with the invoker, in 413. The unique identifier can be used by the issuer 402 when generating certificates. In some embodiments, the unique identifier may be created based on a blockchain identifier of the issuer (fabric ID), however embodiments are not limited thereto.

In response, the chaincode 406 may derive a new issuer identifier in 414 and simulate the transaction against the current state of the blockchain ledger 408, in 415. The simulation ensures that the new issuer identifier 414 is unique. If the simulation is successful in 415, the chaincode 406 forwards the issuer identifier to the blockchain application 404 and the issuer with a success response, in 416. To record the issuer identifier, the issuer 402 may transmit a blockchain transaction to the blockchain peer which is recorded on the blockchain ledger, in 417. For example, the blockchain transaction may include the issuer identifier, a timestamp, and the like. Now that the issuer identifier is recorded to the blockchain ledger 408, it can be accessed by a verifier as described in the example of FIG. 4B.

According to various embodiments, the chaincode 406 may create the issuer identifier 414 by reading values from the blockchain and concatenating the values together. For example, the issuer identifier 414 may include one or more values that are read or otherwise captured by the chaincode 406 and combined in some way, for example, via concatenation, or the like. As one non-limiting example, the issuer identifier 414 may include a prefix (e.g., did:hpass) that is unique among all other issuers that have privileges to issue credentials on the system. Here, the prefix may be created by the system (e.g., a blockchain peer or the like) when the issuer registers with the system. As another example, the issuer identifier 414 may include a hash of a genesis block (i.e., the first block) of the blockchain to which the issuer 402 is onboarded. As another example, the issuer identifier 414 may include a hash of the full issuer identifier in the blockchain fabric. The full issuer identifier may include a membership service provider identifier concatenated with a blockchain fabric identify of the issuer. In one embodiment, the chaincode 406 may create the issuer identifier 414 to include each of the unique prefix, the hash of the genesis block, and the hash of the full issuer identifier which are concatenated together. It should also be appreciated that other features/values may be added or otherwise included in the issuer identifier 414 and embodiments are not limited thereto.

FIG. 4B illustrates a communication process 400B for verifying a scanned certificate according to example embodiments. In this example, a user 430 may have a health certificate that has been converted into a QR code that is stored on a user device (e.g., a mobile application on the user's device, etc.) or a piece of paper. The health certificate may specify that the user has passed a health-related exam, for example, a virus check, or the like. Here, the user 430 brings their device (or piece of paper, etc.) with the QR code displayed thereon within a vicinity of a verifier 432. In 440, the verifier may scan the QR code. In this example, the verifier may be an authority, an employer, an airline, a stadium, or the like, which the user 430 is trying to prove their health with. In 441, the verifier 432 may decode the contents of the machine-readable code which reveals the issuer identifier, the user identifier, the health data, the digital signature added to the certificate, and the like.

In this example, the QR Code represents a visual encoding of health certificate. When an application on the verifier 432 scans the QR code, it transforms the QR code into a string which contains the health data and the issuer identifier. The transformation of the QR code may also reveal other data such as a creation time of the QR code, a schema identifier of the data, an issuer identifier, a digital signature of the issuer, and the health data included in the certificate. In some embodiments, the QR content may depend on the specific application to be implemented (and therefore may or may not contain user information). In particular, for the healthcare use-case application, data may be PII. For this reason, there is the possibility to obfuscate the certificate fields selectively to comply with GDPR.

In 442, the verifier 432 transmits a request for a public key to the blockchain application 404. Here, the request may include the issuer identifier obtained from the scanned QR code. In 443, the blockchain application 404 may retrieve the public key of the issuer from the blockchain ledger 408 based on the issuer identifier received from the blockchain application 404. In 444, the blockchain application 404 may forward the public key to the verifier 432. In 445, the verifier 432 verifies the digital signature of the issuer (created with the issuer's private key) with the public key retrieved from the blockchain ledger 408. If verified, the verifier 432 can trust the data within the decoded QR code, in 446. In this case, the data being accessed proves the health of the user 430 to the verifier 432.

Figure 5:
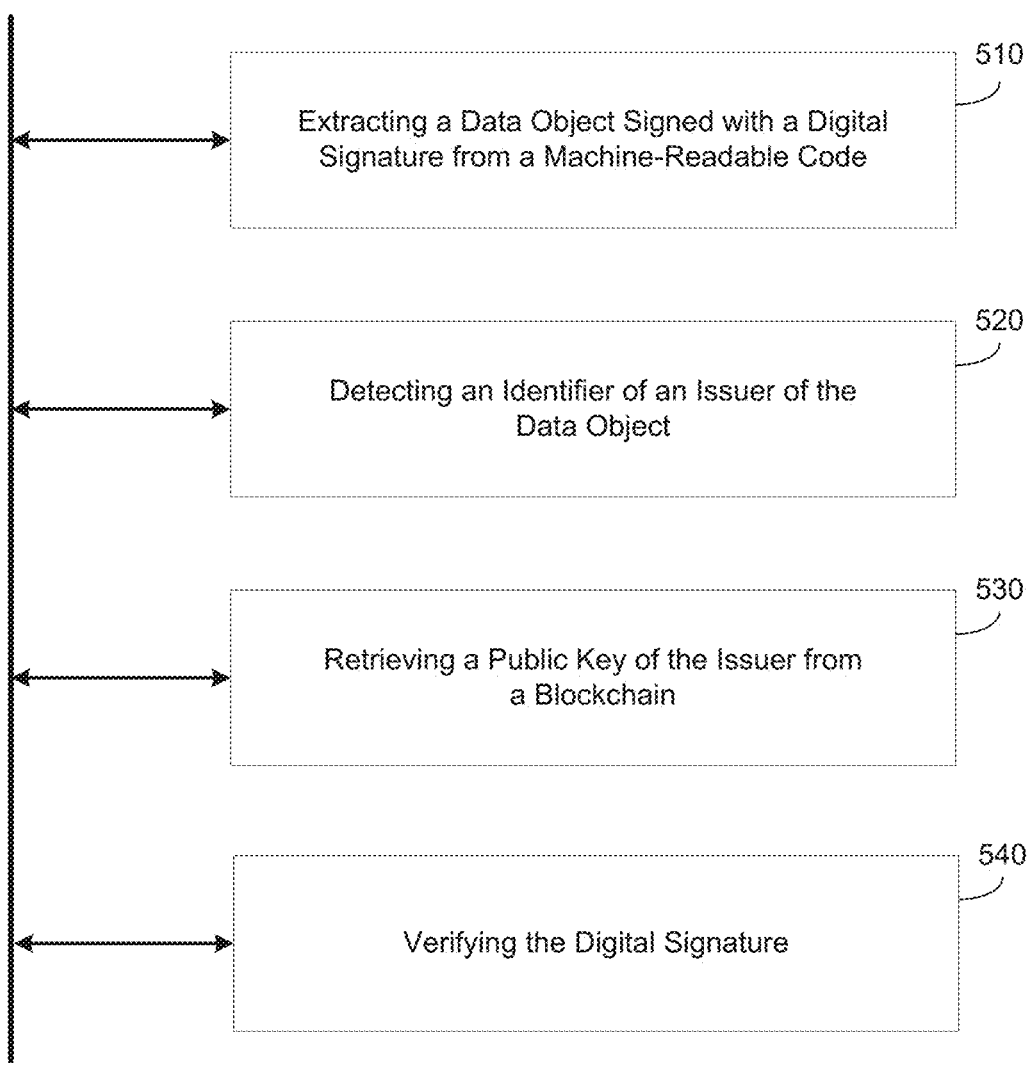
FIG. 5 is a diagram illustrating a method of verifying a certificate via a blockchain according to example embodiments.

FIG. 5 illustrates a method 500 of verifying a certificate via a blockchain according to example embodiments. As a non-limiting example, the method 500 may be performed by a verification device (e.g., smart phone, laptop, computing system, tablet, application, etc.) that interacts with a blockchain ledger, and the like. Referring to FIG. 5, in 510, the method may include extracting a data object from a machine-readable code, where the data object comprises fields of data signed with a digital signature of a private key. For example, the machine-readable code may be a QR code or other barcode. The data object may be a certificate with fields of data values including data of a user. By encoding the certificate into the QR code, the data can remain hidden until scanned by a verification entity.

In 520, the method may include detecting an identifier of an issuer of the data object from the extracted data object. For example, the identifier of the issuer may include a string value that is embedded or otherwise encoded within the machine-readable code by an issuer of the machine-readable code/data object. The issuer identifier may include a text-based or numerical based identifier that uniquely identifies the issuer on a blockchain network which stores a registry of public keys of various issuers.

In 530, the method may include retrieving a public key from a blockchain based on the identifier of the issuer detected from the field of the extracted data object. The retrieving may include transmitting, to a blockchain peer, a request which comprises the identifier of the issuer of the data object, and receiving, from the blockchain peer, the public key. In 540, the method may further include verifying the digital signature of the private key based on the fetched public key. Here, the verification device may decrypt the digital signature of the private key with the public key, and verify the decrypted data.

In some embodiments, the detecting may further include detecting an identifier of a schema associated with the fields of data within the extracted data object, and verifying the schema with the blockchain based on the identifier of the schema. In some embodiments, the extracted data object may include a string value including data values from the fields concatenated together. In some embodiments, the extracting may include scanning a quick response code via an imaging device, where the quick response code comprises the data object encoded therein. In some embodiments, the data object may include a certificate of health issued by the issuer which includes a test result, a user identifier, and a timestamp. In some embodiments, the blockchain may include a registry which includes identities of a plurality of issuers and public keys of the plurality of issuers linked thereto. In some embodiments, the extracting may further include extracting an identity of a user associated with the fields of data which is encoded within the machine readable code.

Figure 6A:
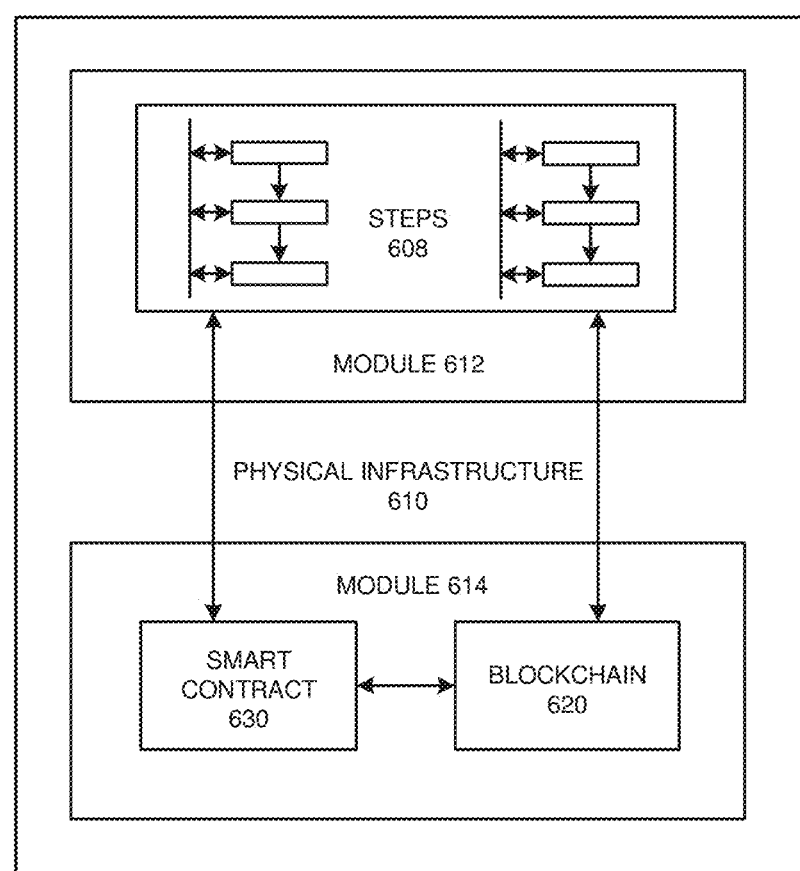
FIG. 6A is a diagram illustrating an example system configured to perform one or more operations described herein, according to example embodiments.

FIG. 6A illustrates an example system 600 that includes a physical infrastructure 610 configured to perform various operations according to example embodiments. Referring to FIG. 6A, the physical infrastructure 610 includes a module 612 and a module 614. The module 614 includes a blockchain 620 and a smart contract 630 (which may reside on the blockchain 620), that may execute any of the operational steps 608 (in module 612) included in any of the example embodiments. The steps/operations 608 may include one or more of the embodiments described or depicted and may represent output or written information that is written or read from one or more smart contracts 630 and/or blockchains 620. The physical infrastructure 610, the module 612, and the module 614 may include one or more computers, servers, processors, memories, and/or wireless communication devices. Further, the module 612 and the module 614 may be a same module.

Figure 6B:
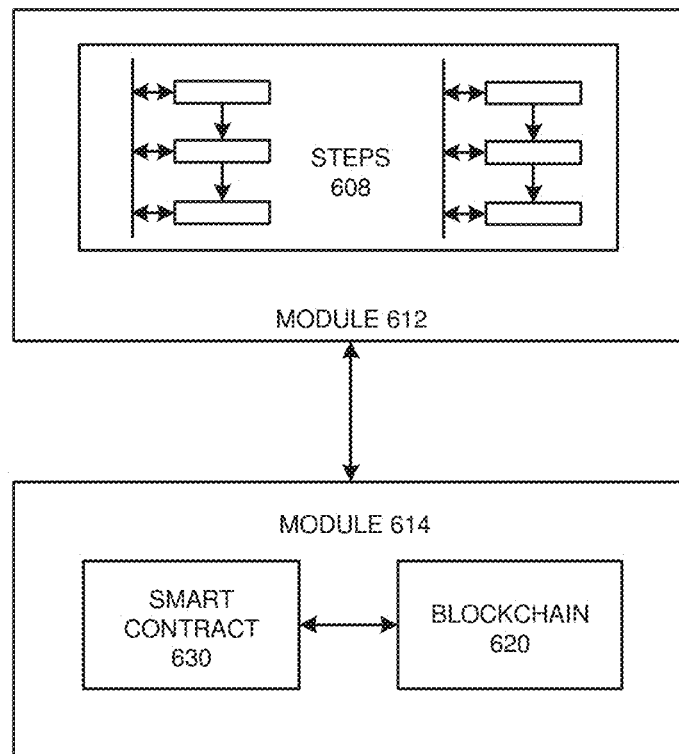
FIG. 6B is a diagram illustrating another example system configured to perform one or more operations described herein, according to example embodiments.

FIG. 6B illustrates another example system 640 configured to perform various operations according to example embodiments. Referring to FIG. 6B, the system 640 includes a module 612 and a module 614. The module 614 includes a blockchain 620 and a smart contract 630 (which may reside on the blockchain 620), that may execute any of the operational steps 608 (in module 612) included in any of the example embodiments. The steps/operations 608 may include one or more of the embodiments described or depicted and may represent output or written information that is written or read from one or more smart contracts 630 and/or blockchains 620. The physical infrastructure 610, the module 612, and the module 614 may include one or more computers, servers, processors, memories, and/or wireless communication devices. Further, the module 612 and the module 614 may be a same module.

Figure 6C:
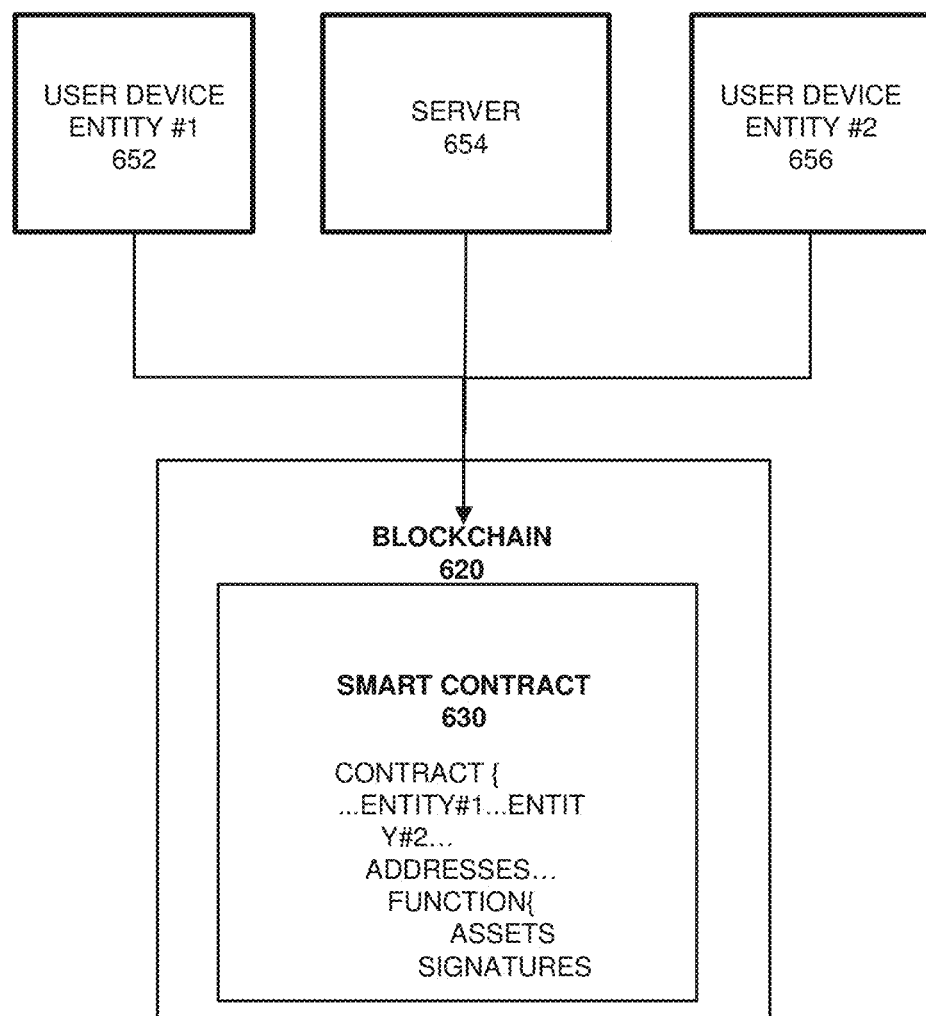
FIG. 6C is a diagram illustrating a further example system configured to utilize a smart contract, according to example embodiments.

FIG. 6C illustrates an example system configured to utilize a smart contract configuration among contracting parties and a mediating server configured to enforce the smart contract terms on the blockchain according to example embodiments. Referring to FIG. 6C, the configuration 650 may represent a communication session, an asset transfer session or a process or procedure that is driven by a smart contract 630 which explicitly identifies one or more user devices 652 and/or 656. The execution, operations and results of the smart contract execution may be managed by a server 654. Content of the smart contract 630 may require digital signatures by one or more of the entities 652 and 656 which are parties to the smart contract transaction. The results of the smart contract execution may be written to a blockchain 620 as a blockchain transaction. The smart contract 630 resides on the blockchain 620 which may reside on one or more computers, servers, processors, memories, and/or wireless communication devices.

Figure 6D:
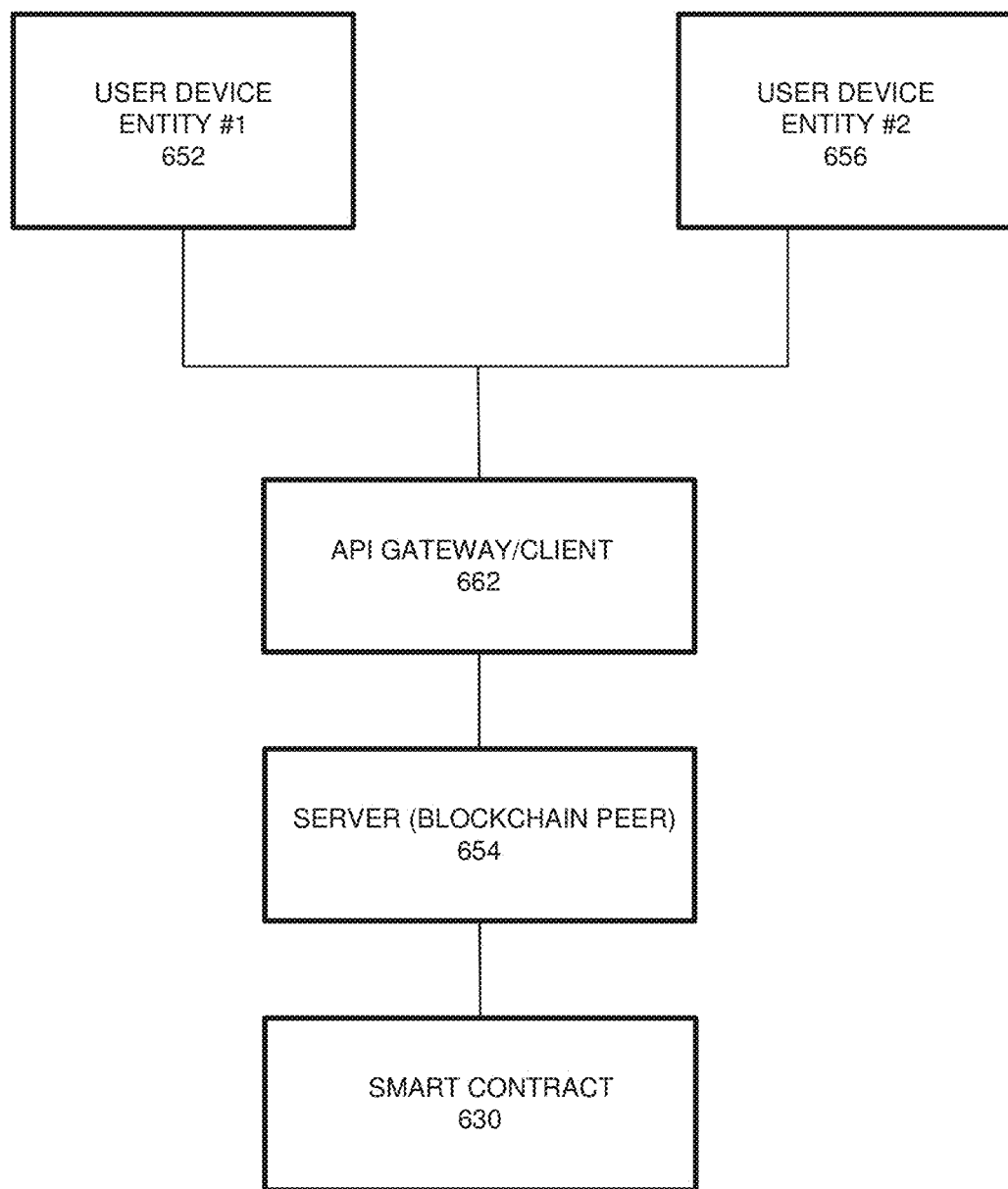
FIG. 6D is a diagram illustrating yet another example system configured to utilize a blockchain, according to example embodiments.

FIG. 6D illustrates a system 660 including a blockchain, according to example embodiments. Referring to the example of FIG. 6D, an application programming interface (API) gateway 662 provides a common interface for accessing blockchain logic (e.g., smart contract 630 or other chaincode) and data (e.g., distributed ledger, etc.). In this example, the API gateway 662 is a common interface for performing transactions (invoke, queries, etc.) on the blockchain by connecting one or more entities 652 and 656 to a blockchain peer (i.e., server 654). Here, the server 654 is a blockchain network peer component that holds a copy of the world state and a distributed ledger allowing clients 652 and 656 to query data on the world state as well as submit transactions into the blockchain network where, depending on the smart contract 630 and endorsement policy, endorsing peers will run the smart contracts 630.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components.

Figure 7A:
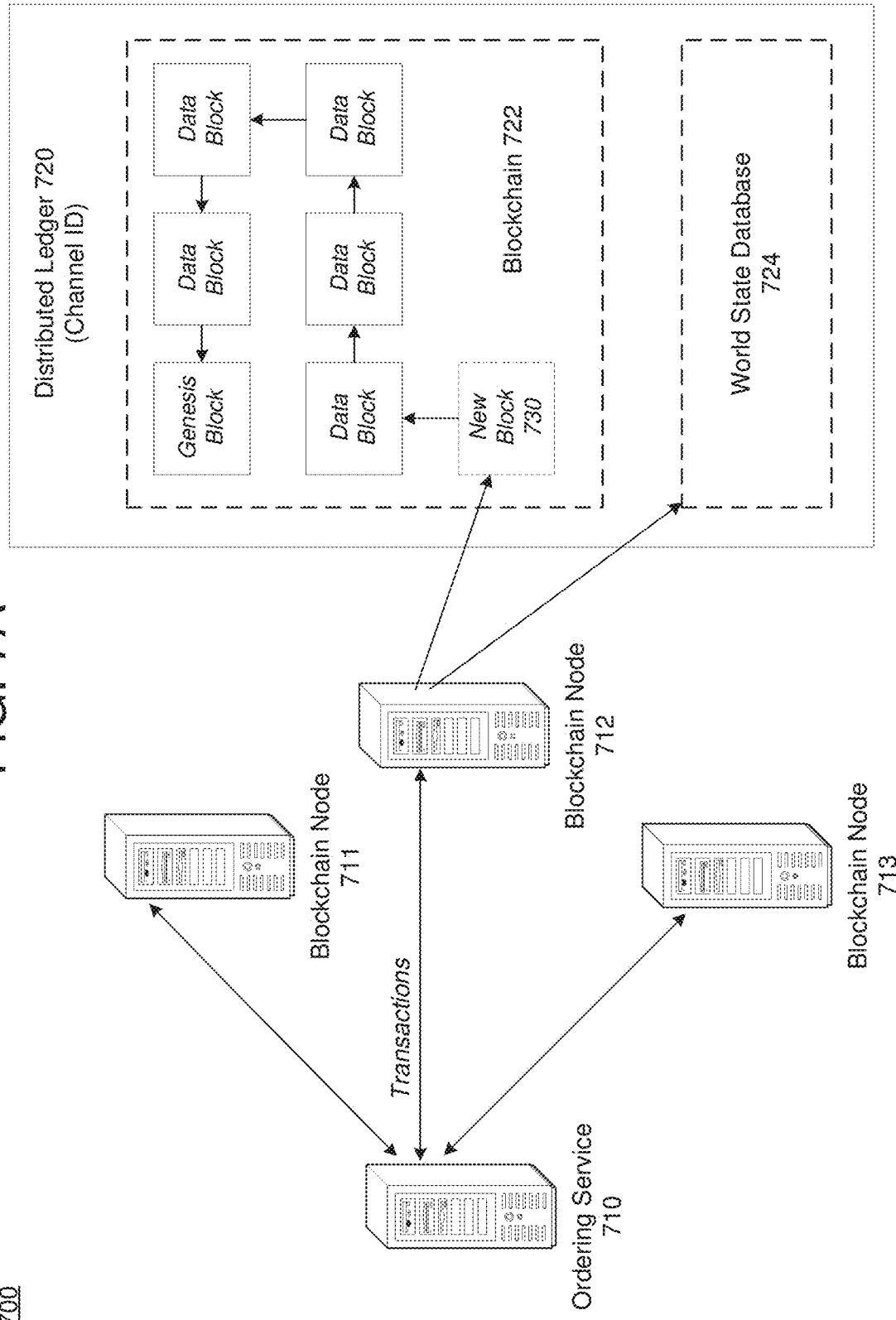
FIG. 7A is a diagram illustrating a process of a new block being added to a distributed ledger, according to example embodiments.
Figure 7B:
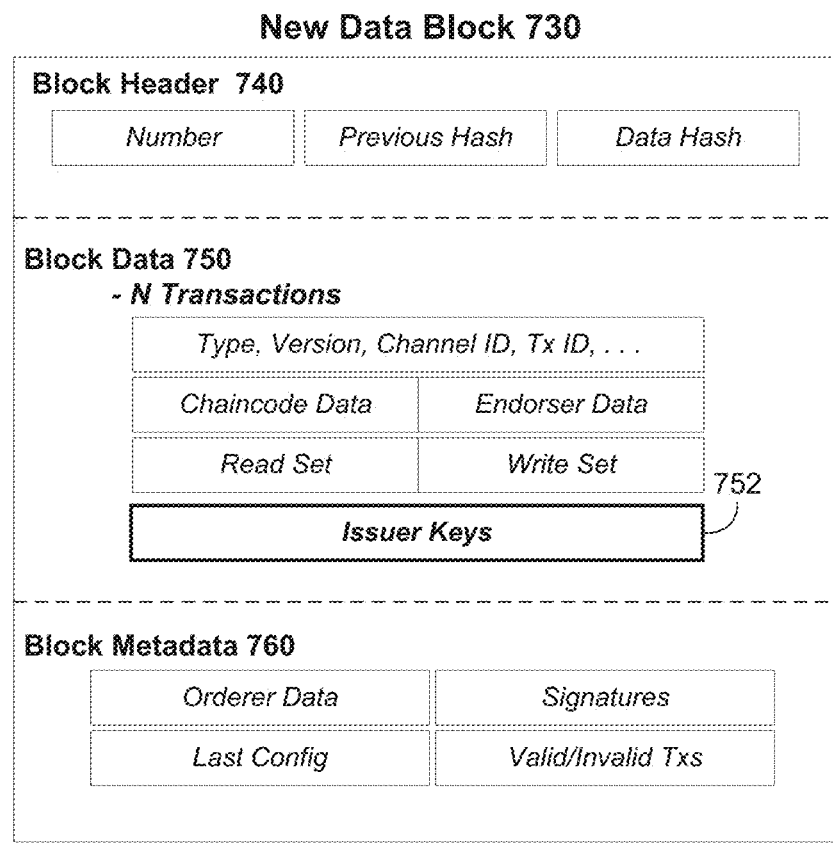
FIG. 7B is a diagram illustrating data contents of a new data block, according to example embodiments.

FIG. 7A illustrates a process 700 of a new block being added to a distributed ledger 720, according to example embodiments, and FIG. 7B illustrates contents of a new data block structure 730 for blockchain, according to example embodiments. Referring to FIG. 7A, clients (not shown) may submit transactions to blockchain nodes 711, 712, and/or 713. Clients may be instructions received from any source to enact activity on the blockchain 720. As an example, clients may be applications that act on behalf of a requester, such as a device, person or entity to propose transactions for the blockchain. The plurality of blockchain peers (e.g., blockchain nodes 711, 712, and 713) may maintain a state of the blockchain network and a copy of the distributed ledger 720. Different types of blockchain nodes/peers may be present in the blockchain network including endorsing peers which simulate and endorse transactions proposed by clients and committing peers which verify endorsements, validate transactions, and commit transactions to the distributed ledger 720. In this example, the blockchain nodes 711, 712, and 713 may perform the role of endorser node, committer node, or both.

The distributed ledger 720 includes a blockchain which stores immutable, sequenced records in blocks, and a state database 724 (current world state) maintaining a current state of the blockchain 722. One distributed ledger 720 may exist per channel and each peer maintains its own copy of the distributed ledger 720 for each channel of which they are a member. The blockchain 722 is a transaction log, structured as hash-linked blocks where each block contains a sequence of N transactions. Blocks may include various components such as shown in FIG. 7B. The linking of the blocks (shown by arrows in FIG. 7A) may be generated by adding a hash of a prior block's header within a block header of a current block. In this way, all transactions on the blockchain 722 are sequenced and cryptographically linked together preventing tampering with blockchain data without breaking the hash links. Furthermore, because of the links, the latest block in the blockchain 722 represents every transaction that has come before it. The blockchain 722 may be stored on a peer file system (local or attached storage), which supports an append-only blockchain workload.

The current state of the blockchain 722 and the distributed ledger 722 may be stored in the state database 724. Here, the current state data represents the latest values for all keys ever included in the chain transaction log of the blockchain 722. Chaincode invocations execute transactions against the current state in the state database 724. To make these chaincode interactions extremely efficient, the latest values of all keys are stored in the state database 724. The state database 724 may include an indexed view into the transaction log of the blockchain 722, it can therefore be regenerated from the chain at any time. The state database 724 may automatically get recovered (or generated if needed) upon peer startup, before transactions are accepted.

Endorsing nodes receive transactions from clients and endorse the transaction based on simulated results. Endorsing nodes hold smart contracts which simulate the transaction proposals. When an endorsing node endorses a transaction, the endorsing nodes creates a transaction endorsement which is a signed response from the endorsing node to the client application indicating the endorsement of the simulated transaction. The method of endorsing a transaction depends on an endorsement policy which may be specified within chaincode. An example of an endorsement policy is "the majority of endorsing peers must endorse the transaction". Different channels may have different endorsement policies. Endorsed transactions are forward by the client application to ordering service 710.

The ordering service 710 accepts endorsed transactions, orders them into a block, and delivers the blocks to the committing peers. For example, the ordering service 710 may initiate a new block when a threshold of transactions has been reached, a timer times out, or another condition. In the example of FIG. 7A, blockchain node 712 is a committing peer that has received a new data new data block 730 for storage on blockchain 720. The first block in the blockchain may be referred to as a genesis block which includes information about the blockchain, its members, the data stored therein, etc.

The ordering service 710 may be made up of a cluster of orderers. The ordering service 710 does not process transactions, smart contracts, or maintain the shared ledger. Rather, the ordering service 710 may accept the endorsed transactions and specifies the order in which those transactions are committed to the distributed ledger 720. The architecture of the blockchain network may be designed such that the specific implementation of 'ordering' (e.g., Solo, Kafka, BFT, etc.) becomes a pluggable component.

Transactions are written to the distributed ledger 720 in a consistent order. The order of transactions is established to ensure that the updates to the state database 724 are valid when they are committed to the network. Unlike a cryptocurrency blockchain system (e.g., Bitcoin, etc.) where ordering occurs through the solving of a cryptographic puzzle, or mining, in this example the parties of the distributed ledger 720 may choose the ordering mechanism that best suits that network.

When the ordering service 710 initializes a new data block 730, the new data block 730 may be broadcast to committing peers (e.g., blockchain nodes 711, 712, and 713). In response, each committing peer validates the transaction within the new data block 730 by checking to make sure that the read set and the write set still match the current world state in the state database 724. Specifically, the committing peer can determine whether the read data that existed when the endorsers simulated the transaction is identical to the current world state in the state database 724. When the committing peer validates the transaction, the transaction is written to the blockchain 722 on the distributed ledger 720, and the state database 724 is updated with the write data from the read-write set. If a transaction fails, that is, if the committing peer finds that the read-write set does not match the current world state in the state database 724, the transaction ordered into a block will still be included in that block, but it will be marked as invalid, and the state database 724 will not be updated.

Referring to FIG. 7B, a new data block 730 (also referred to as a data block) that is stored on the blockchain 722 of the distributed ledger 720 may include multiple data segments such as a block header 740, block data 750 (block data section), and block metadata 760. It should be appreciated that the various depicted blocks and their contents, such as new data block 730 and its contents, shown in FIG. 7B are merely examples and are not meant to limit the scope of the example embodiments. In a conventional block, the data section may store transactional information of N transaction(s) (e.g., 1, 10, 100, 500, 1000, 2000, 3000, etc.) within the block data 750.

The new data block 730 may include a link to a previous block (e.g., on the blockchain 722 in FIG. 7A) within the block header 740. In particular, the block header 740 may include a hash of a previous block's header. The block header 740 may also include a unique block number, a hash of the block data 750 of the new data block 730, and the like. The block number of the new data block 730 may be unique and assigned in various orders, such as an incremental/sequential order starting from zero.

According to various embodiments, the block data 750 may store public keys of issuers (issuer keys 752) that are registered in the blockchain system. For example, the issuer keys 752 may be paired with an issuer ID. Each issuer may store their issuer ID and public key on the blockchain during an onboarding process. According to various embodiments, the issuer keys 752 can be stored in various blockchain transactions within an immutable log of blocks on the distributed ledger 720. Some of the benefits of storing the issuer keys 752 on the blockchain are reflected in the various embodiments disclosed and depicted herein. Although in FIG. 7B, the issuer keys 752 are depicted in the block data 750, in other embodiments, the issuer keys 752 may be located in the block header 740 or the block metadata 760.

The block metadata 760 may store multiple fields of metadata (e.g., as a byte array, etc.). Metadata fields may include signature on block creation, a reference to a last configuration block, a transaction filter identifying valid and invalid transactions within the block, last offset persisted of an ordering service that ordered the block, and the like. The signature, the last configuration block, and the orderer metadata may be added by the ordering service 710. Meanwhile, a committer of the block (such as blockchain node 712) may add validity/invalidity information based on an endorsement policy, verification of read/write sets, and the like. The transaction filter may include a byte array of a size equal to the number of transactions that are included in the block data 750 and a validation code identifying whether a transaction was valid/invalid.

Figure 7C:
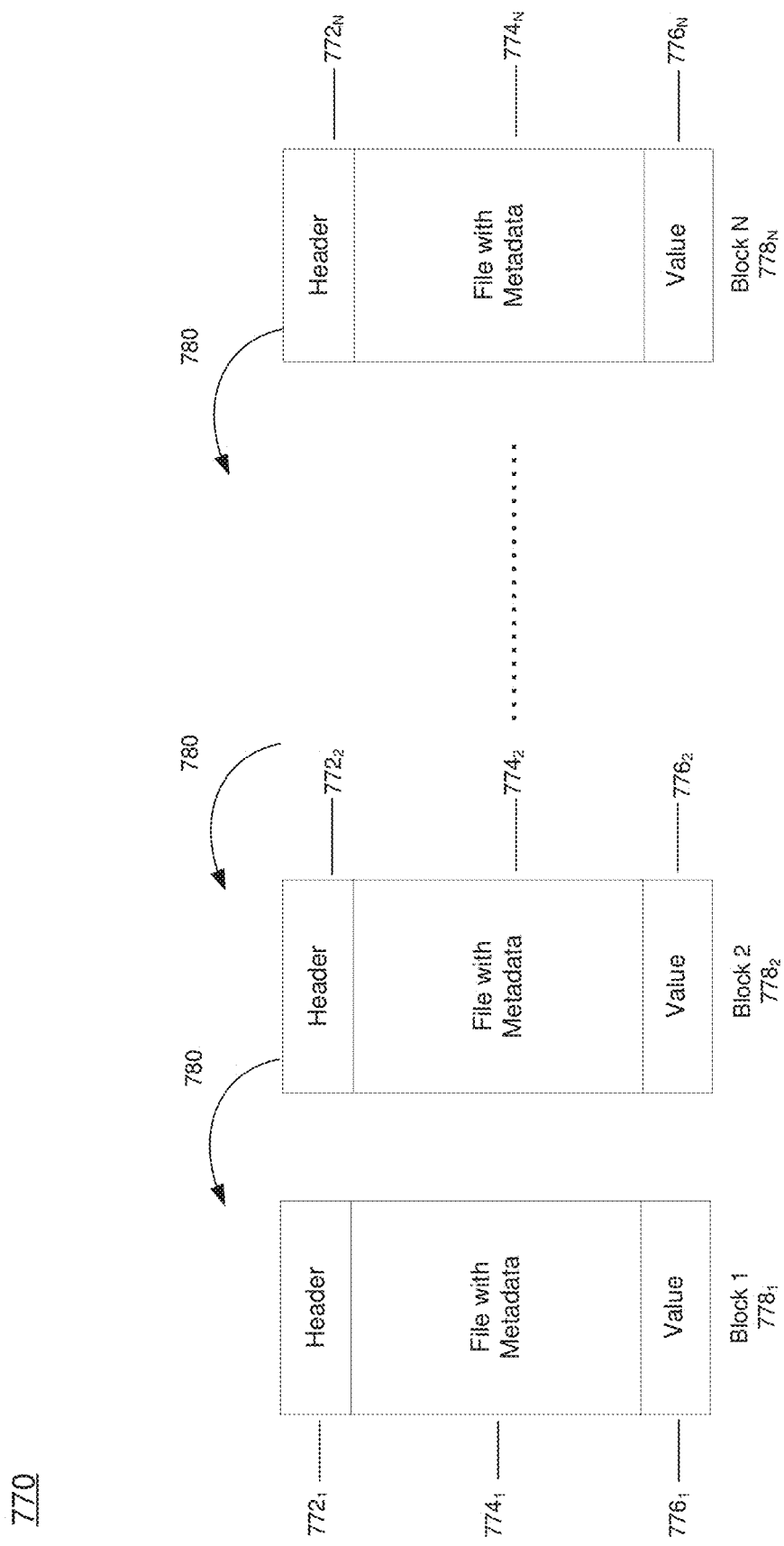
FIG. 7C is a diagram illustrating a blockchain for digital content, according to example embodiments.

FIG. 7C illustrates an embodiment of a blockchain 770 for digital content in accordance with the embodiments described herein. The digital content may include one or more files and associated information. The files may include media, images, video, audio, text, links, graphics, animations, web pages, documents, or other forms of digital content. The immutable, append-only aspects of the blockchain serve as a safeguard to protect the integrity, validity, and authenticity of the digital content, making it suitable use in legal proceedings where admissibility rules apply or other settings where evidence is taken into consideration or where the presentation and use of digital information is otherwise of interest. In this case, the digital content may be referred to as digital evidence.

The blockchain may be formed in various ways. In one embodiment, the digital content may be included in and accessed from the blockchain itself. For example, each block of the blockchain may store a hash value of reference information (e.g., header, value, etc.) along the associated digital content. The hash value and associated digital content may then be encrypted together. Thus, the digital content of each block may be accessed by decrypting each block in the blockchain, and the hash value of each block may be used as a basis to reference a previous block. This may be illustrated as follows:

| Block 1 | Block 2 | ... | Block N |
|---|---|---|---|
| Hash Value 1 | Hash Value 2 | | Hash Value N |
| Digital Content 1 | Digital Content 2 | | Digital Content N |

In one embodiment, the digital content may be not included in the blockchain. For example, the blockchain may store the encrypted hashes of the content of each block without any of the digital content. The digital content may be stored in another storage area or memory address in association with the hash value of the original file. The other storage area may be the same storage device used to store the blockchain or may be a different storage area or even a separate relational database. The digital content of each block may be referenced or accessed by obtaining or querying the hash value of a block of interest and then looking up that has value in the storage area, which is stored in correspondence with the actual digital content. This operation may be performed, for example, a database gatekeeper. This may be illustrated as follows:

| Blockchain | Storage Area |
|---|---|
| Block 1 Hash Value | Block 1 Hash Value . . . Content |
| . | . |
| . | . |
| . | . |
| Block N Hash Value | Block N Hash Value . . . Content |

In the example embodiment of FIG. 7C, the blockchain 770 includes a number of blocks $778_1$, $778_2$, . . . $778_N$ cryptographically linked in an ordered sequence, where $N \geq 1$. The encryption used to link the blocks $778_1$, $778_2, \ldots 778_N$ may be any of a number of keyed or un-keyed Hash functions. In one embodiment, the blocks $778_1$, $778_2, \ldots 778_N$ are subject to a hash function which produces n-bit alphanumeric outputs (where n is 256 or another number) from inputs that are based on information in the blocks. Examples of such a hash function include, but are not limited to, a SHA-type (SHA stands for Secured Hash Algorithm) algorithm, Merkle-Damgard algorithm, HAIFA algorithm, Merkle-tree algorithm, nonce-based algorithm, and a non-collision-resistant PRF algorithm. In another embodiment, the blocks $778_1$, $778_2$, . . . , $778_N$ may be cryptographically linked by a function that is different from a hash function. For purposes of illustration, the following description is made with reference to a hash function, e.g., SHA-2.

Each of the blocks $778_1, 778_2, \ldots, 778_N$ in the blockchain includes a header, a version of the file, and a value. The header and the value are different for each block as a result of hashing in the blockchain. In one embodiment, the value may be included in the header. As described in greater detail below, the version of the file may be the original file or a different version of the original file.

The first block $778_1$ in the blockchain is referred to as the genesis block and includes the header $772_1$, original file $774_1$, and an initial value $776_1$. The hashing scheme used for the genesis block, and indeed in all subsequent blocks, may vary. For example, all the information in the first block $778_1$ may be hashed together and at one time, or each or a portion of the information in the first block $778_1$ may be separately hashed and then a hash of the separately hashed portions may be performed.

The header $772_1$ may include one or more initial parameters, which, for example, may include a version number, timestamp, nonce, root information, difficulty level, consensus protocol, duration, media format, source, descriptive keywords, and/or other information associated with original file $774_1$ and/or the blockchain. The header $772_1$ may be generated automatically (e.g., by blockchain network managing software) or manually by a blockchain participant. Unlike the header in other blocks $778_2$ to $778_N$ in the blockchain, the header $772_1$ in the genesis block does not reference a previous block, simply because there is no previous block.

The original file $774_1$ in the genesis block may be, for example, data as captured by a device with or without processing prior to its inclusion in the blockchain. The original file $774_1$ is received through the interface of the system from the device, media source, or node. The original file $774_1$ is associated with metadata, which, for example, may be generated by a user, the device, and/or the system processor, either manually or automatically. The metadata may be included in the first block $778_1$ in association with the original file $774_1$.

The value $776_1$ in the genesis block is an initial value generated based on one or more unique attributes of the original file $774_1$. In one embodiment, the one or more unique attributes may include the hash value for the original file $774_1$, metadata for the original file $774_1$, and other information associated with the file. In one implementation, the initial value $776_1$ may be based on the following unique attributes:

1) SHA-2 computed hash value for the original file
2) originating device ID
3) starting timestamp for the original file
4) initial storage location of the original file
5) blockchain network member ID for software to currently control the original file and associated metadata The other blocks $778_2$ to $778_N$ in the blockchain also have headers, files, and values. However, unlike the first block $772_1$, each of the headers $772_2$ to $772_N$ in the other blocks includes the hash value of an immediately preceding block. The hash value of the immediately preceding block may be just the hash of the header of the previous block or may be the hash value of the entire previous block. By including the hash value of a preceding block in each of the remaining blocks, a trace can be performed from the Nth block back to the genesis block (and the associated original file) on a block-by-block basis, as indicated by arrows 780, to establish an auditable and immutable chain-of-custody.

Each of the header $772_2$ to $772_N$ in the other blocks may also include other information, e.g., version number, timestamp, nonce, root information, difficulty level, consensus protocol, and/or other parameters or information associated with the corresponding files and/or the blockchain in general.

The files $774_2$ to $774_N$ in the other blocks may be equal to the original file or may be a modified version of the original file in the genesis block depending, for example, on the type of processing performed. The type of processing performed may vary from block to block. The processing may involve, for example, any modification of a file in a preceding block, such as redacting information or otherwise changing the content of, taking information away from, or adding or appending information to the files.

Additionally, or alternatively, the processing may involve merely copying the file from a preceding block, changing a storage location of the file, analyzing the file from one or more preceding blocks, moving the file from one storage or memory location to another, or performing action relative to the file of the blockchain and/or its associated metadata. Processing which involves analyzing a file may include, for example, appending, including, or otherwise associating various analytics, statistics, or other information associated with the file.

The values in each of the other blocks $776_2$ to $776_N$ in the other blocks are unique values and are all different as a result of the processing performed. For example, the value in any one block corresponds to an updated version of the value in the previous block. The update is reflected in the hash of the block to which the value is assigned. The values of the blocks therefore provide an indication of what processing was performed in the blocks and also permit a tracing through the blockchain back to the original file. This tracking confirms the chain-of-custody of the file throughout the entire blockchain.

For example, consider the case where portions of the file in a previous block are redacted, blocked out, or pixelated in order to protect the identity of a person shown in the file. In this case, the block including the redacted file will include metadata associated with the redacted file, e.g., how the redaction was performed, who performed the redaction, timestamps where the redaction(s) occurred, etc. The metadata may be hashed to form the value. Because the metadata for the block is different from the information that was hashed to form the value in the previous block, the values are different from one another and may be recovered when decrypted.

Figure 7D:
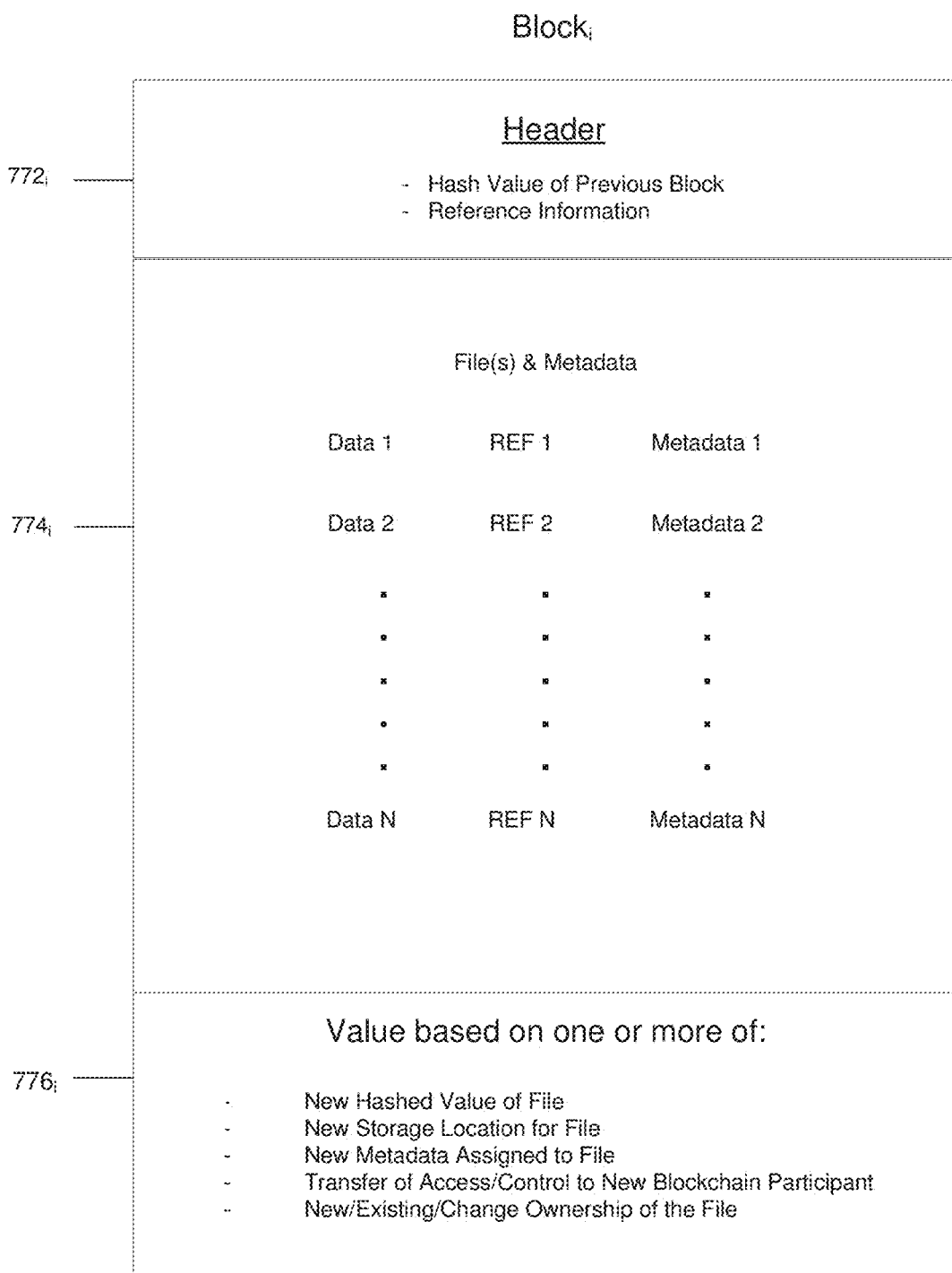
FIG. 7D is a diagram illustrating a block which may represent the structure of blocks in the blockchain, according to example embodiments.

In one embodiment, the value of a previous block may be updated (e.g., a new hash value computed) to form the value of a current block when any one or more of the following occurs. The new hash value may be computed by hashing all or a portion of the information noted below, in this example embodiment.

a) new SHA-2 computed hash value if the file has been processed in any way (e.g., if the file was redacted, copied, altered, accessed, or some other action was taken)
b) new storage location for the file
c) new metadata identified associated with the file
d) transfer of access or control of the file from one blockchain participant to another blockchain participant FIG. 7D illustrates an embodiment of a block which may represent the structure of the blocks in the blockchain 790 in accordance with one embodiment. The block, Block$_i$, includes a header 772$_i$, a file 774$_i$, and a value 776$_i$.

The header 772$_i$ includes a hash value of a previous block Block$_{i-1}$ and additional reference information, which, for example, may be any of the types of information (e.g., header information including references, characteristics, parameters, etc.) discussed herein. All blocks reference the hash of a previous block except, of course, the genesis block. The hash value of the previous block may be just a hash of the header in the previous block or a hash of all or a portion of the information in the previous block, including the file and metadata.

The file 774$_i$ includes a plurality of data, such as Data 1, Data 2, . . . , Data N in sequence. The data are tagged with Metadata 1, Metadata 2, . . . , Metadata N which describe the content and/or characteristics associated with the data. For example, the metadata for each data may include information to indicate a timestamp for the data, process the data, keywords indicating the persons or other content depicted in the data, and/or other features that may be helpful to establish the validity and content of the file as a whole, and particularly its use a digital evidence, for example, as described in connection with an embodiment discussed below. In addition to the metadata, each data may be tagged with reference REF$_1$, REF$_2$, . . . , REF$_N$ to a previous data to prevent tampering, gaps in the file, and sequential reference through the file.

Once the metadata is assigned to the data (e.g., through a smart contract), the metadata cannot be altered without the hash changing, which can easily be identified for invalidation. The metadata, thus, creates a data log of information that may be accessed for use by participants in the blockchain.

The value 776$_i$ is a hash value or other value computed based on any of the types of information previously discussed. For example, for any given block Block$_i$, the value for that block may be updated to reflect the processing that was performed for that block, e.g., new hash value, new storage location, new metadata for the associated file, transfer of control or access, identifier, or other action or information to be added. Although the value in each block is shown to be separate from the metadata for the data of the file and header, the value may be based, in part or whole, on this metadata in another embodiment.

Once the blockchain 770 is formed, at any point in time, the immutable chain-of-custody for the file may be obtained by querying the blockchain for the transaction history of the values across the blocks. This query, or tracking procedure, may begin with decrypting the value of the block that is most currently included (e.g., the last (N$^{th}$) block), and then continuing to decrypt the value of the other blocks until the genesis block is reached and the original file is recovered. The decryption may involve decrypting the headers and files and associated metadata at each block, as well.

Decryption is performed based on the type of encryption that took place in each block. This may involve the use of private keys, public keys, or a public key-private key pair. For example, when asymmetric encryption is used, blockchain participants or a processor in the network may generate a public key and private key pair using a predetermined algorithm. The public key and private key are associated with each other through some mathematical relationship. The public key may be distributed publicly to serve as an address to receive messages from other users, e.g., an IP address or home address. The private key is kept secret and used to digitally sign messages sent to other blockchain participants. The signature is included in the message so that the recipient can verify using the public key of the sender. This way, the recipient can be sure that only the sender could have sent this message.

Generating a key pair may be analogous to creating an account on the blockchain, but without having to actually register anywhere. Also, every transaction that is executed on the blockchain is digitally signed by the sender using their private key. This signature ensures that only the owner of the account can track and process (if within the scope of permission determined by a smart contract) the file of the blockchain.

FIGS. 8A and 8B illustrate additional examples of use cases for blockchain which may be incorporated and used herein. In particular, FIG. 8A illustrates an example 800 of a blockchain 810 which stores machine learning (artificial intelligence) data. Machine learning relies on vast quantities of historical data (or training data) to build predictive models for accurate prediction on new data. Machine learning software (e.g., neural networks, etc.) can often sift through millions of records to unearth non-intuitive patterns.

In the example of FIG. 8A, a host platform 820 builds and deploys a machine learning model for predictive monitoring of assets 830. Here, the host platform 820 may be a cloud platform, an industrial server, a web server, a personal computer, a user device, and the like. Assets 830 can be any type of asset (e.g., machine or equipment, etc.) such as an aircraft, locomotive, turbine, medical machinery and equipment, oil and gas equipment, boats, ships, vehicles, and the like. As another example, assets 830 may be non-tangible assets such as stocks, currency, digital coins, insurance, or the like.

The blockchain 810 can be used to significantly improve both a training process 802 of the machine learning model and a predictive process 804 based on a trained machine learning model. For example, in 802, rather than requiring a data scientist/engineer or other user to collect the data, historical data may be stored by the assets 830 themselves (or through an intermediary, not shown) on the blockchain 810. This can significantly reduce the collection time needed by the host platform 820 when performing predictive model training. For example, using smart contracts, data can be directly and reliably transferred straight from its place of origin to the blockchain 810. By using the blockchain 810 to ensure the security and ownership of the collected data, smart contracts may directly send the data from the assets to the individuals that use the data for building a machine learning model. This allows for sharing of data among the assets 830.

The collected data may be stored in the blockchain 810 based on a consensus mechanism. The consensus mechanism pulls in (permissioned nodes) to ensure that the data being recorded is verified and accurate. The data recorded is time-stamped, cryptographically signed, and immutable. It is therefore auditable, transparent, and secure. Adding IoT devices which write directly to the blockchain can, in certain cases (i.e. supply chain, healthcare, logistics, etc.), increase both the frequency and accuracy of the data being recorded.

Furthermore, training of the machine learning model on the collected data may take rounds of refinement and testing by the host platform 820. Each round may be based on additional data or data that was not previously considered to help expand the knowledge of the machine learning model. In 802, the different training and testing steps (and the data associated therewith) may be stored on the blockchain 810 by the host platform 820. Each refinement of the machine learning model (e.g., changes in variables, weights, etc.) may be stored on the blockchain 810. This provides verifiable proof of how the model was trained and what data was used to train the model. Furthermore, when the host platform 820 has achieved a finally trained model, the resulting model may be stored on the blockchain 810.

After the model has been trained, it may be deployed to a live environment where it can make predictions/decisions based on the execution of the final trained machine learning model. For example, in 804, the machine learning model may be used for condition-based maintenance (CBM) for an asset such as an aircraft, a wind turbine, a healthcare machine, and the like. In this example, data fed back from the asset 830 may be input the machine learning model and used to make event predictions such as failure events, error codes, and the like. Determinations made by the execution of the machine learning model at the host platform 820 may be stored on the blockchain 810 to provide auditable/verifiable proof. As one non-limiting example, the machine learning model may predict a future breakdown/failure to a part of the asset 830 and create alert or a notification to replace the part. The data behind this decision may be stored by the host platform 820 on the blockchain 810. In one embodiment the features and/or the actions described and/or depicted herein can occur on or with respect to the blockchain 810.

New transactions for a blockchain can be gathered together into a new block and added to an existing hash value. This is then encrypted to create a new hash for the new block. This is added to the next list of transactions when they are encrypted, and so on. The result is a chain of blocks that each contain the hash values of all preceding blocks. Computers that store these blocks regularly compare their hash values to ensure that they are all in agreement. Any computer that does not agree, discards the records that are causing the problem. This approach is good for ensuring tamper-resistance of the blockchain, but it is not perfect.

One way to game this system is for a dishonest user to change the list of transactions in their favor, but in a way that leaves the hash unchanged. This can be done by brute force, in other words by changing a record, encrypting the result, and seeing whether the hash value is the same. And if not, trying again and again and again until it finds a hash that matches. The security of blockchains is based on the belief that ordinary computers can only perform this kind of brute force attack over time scales that are entirely impractical, such as the age of the universe. By contrast, quantum computers are much faster (1000 s of times faster) and consequently pose a much greater threat.

FIG. 8B illustrates an example 850 of a quantum-secure blockchain 852 which implements quantum key distribution (QKD) to protect against a quantum computing attack. In this example, blockchain users can verify each other's identities using QKD. This sends information using quantum particles such as photons, which cannot be copied by an eavesdropper without destroying them. In this way, a sender and a receiver through the blockchain can be sure of each other's identity.

In the example of FIG. 8B, four users are present 854, 856, 858, and 860. Each of pair of users may share a secret key 862 (i.e., a QKD) between themselves. Since there are four nodes in this example, six pairs of nodes exists, and therefore six different secret keys 862 are used including $QKD_{AB}$, $QKD_{AC}$, $QKD_{AD}$, $QKD_{BC}$, $QKD_{BD}$, and $QKD_{CD}$. Each pair can create a QKD by sending information using quantum particles such as photons, which cannot be copied by an eavesdropper without destroying them. In this way, a pair of users can be sure of each other's identity.

The operation of the blockchain 852 is based on two procedures (i) creation of transactions, and (ii) construction of blocks that aggregate the new transactions. New transactions may be created similar to a traditional blockchain network. Each transaction may contain information about a sender, a receiver, a time of creation, an amount (or value) to be transferred, a list of reference transactions that justifies the sender has funds for the operation, and the like. This transaction record is then sent to all other nodes where it is entered into a pool of unconfirmed transactions. Here, two parties (i.e., a pair of users from among 854-860) authenticate the transaction by providing their shared secret key 862 (QKD). This quantum signature can be attached to every transaction making it exceedingly difficult to tamper with. Each node checks their entries with respect to a local copy of the blockchain 852 to verify that each transaction has sufficient funds. However, the transactions are not yet confirmed.

Rather than perform a traditional mining process on the blocks, the blocks may be created in a decentralized manner using a broadcast protocol. At a predetermined period of time (e.g., seconds, minutes, hours, etc.) the network may apply the broadcast protocol to any unconfirmed transaction thereby to achieve a Byzantine agreement (consensus) regarding a correct version of the transaction. For example, each node may possess a private value (transaction data of that particular node). In a first round, nodes transmit their private values to each other. In subsequent rounds, nodes communicate the information they received in the previous round from other nodes. Here, honest nodes are able to create a complete set of transactions within a new block. This new block can be added to the blockchain 852. In one embodiment the features and/or the actions described and/or depicted herein can occur on or with respect to the blockchain 852.

Figure 9:
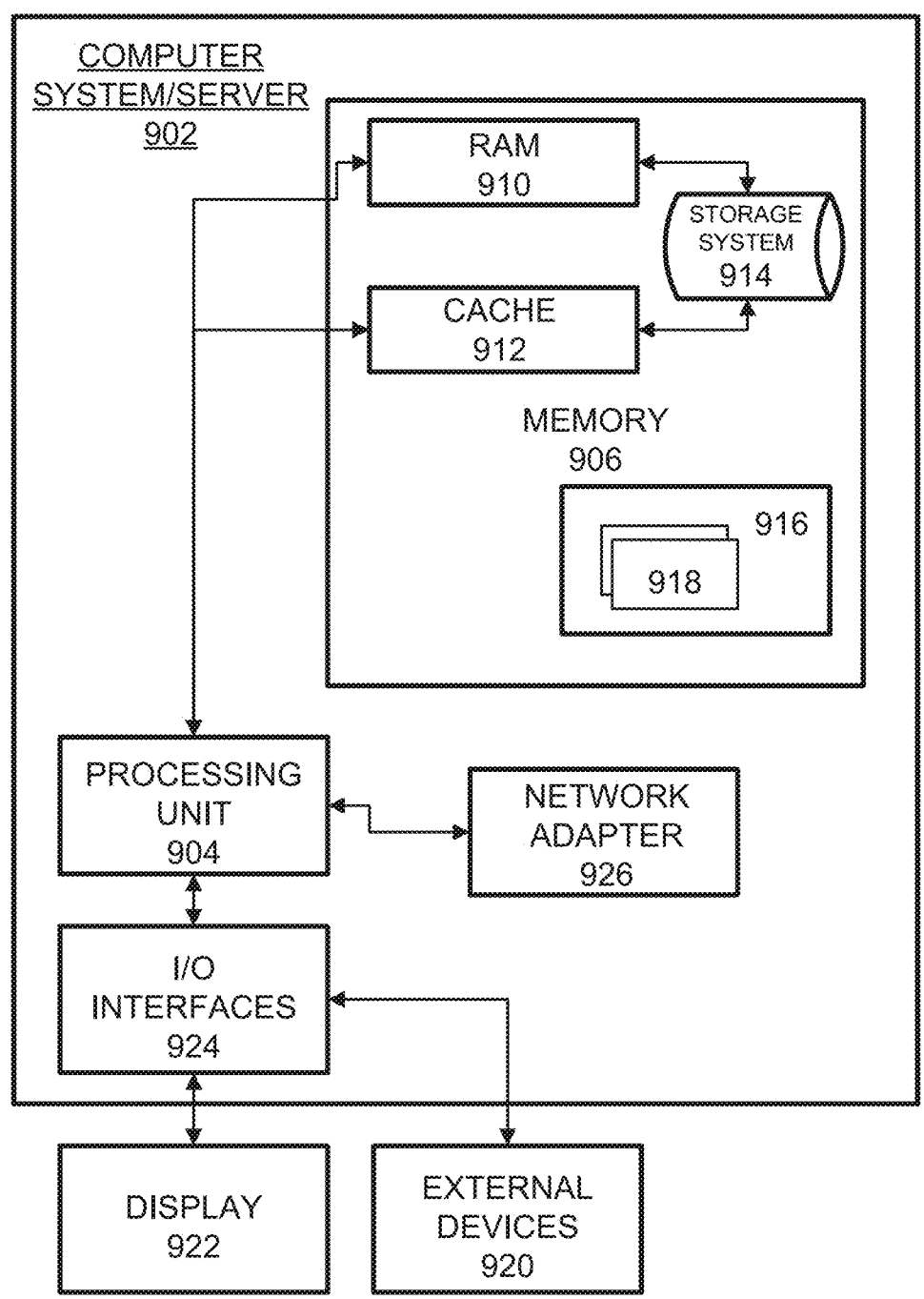
FIG. 9 is a diagram illustrating an example system that supports one or more of the example embodiments.

FIG. 9 illustrates an example system 900 that supports one or more of the example embodiments described and/or depicted herein. The system 900 comprises a computer system/server 902, which is operational with numerous other general purpose or special purpose computing system environments or configurations. Examples of well-known computing systems, environments, and/or configurations that may be suitable for use with computer system/server 902 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 902 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 902 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 902 in cloud computing node 900 is shown in the form of a general-purpose computing device. The components of computer system/server 902 may include, but are not limited to, one or more processors or processing units 904, a system memory 906, and a bus that couples various system components including system memory 906 to processor 904.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 902 typically includes a variety of computer system readable media. Such media may be any available media that is accessible by computer system/server 902, and it includes both volatile and non-volatile media, removable and non-removable media. System memory 906, in one embodiment, implements the flow diagrams of the other figures. The system memory 906 can include computer system readable media in the form of volatile memory, such as random-access memory (RAM) 910 and/or cache memory 912. Computer system/server 902 may further include other removable/non-removable, volatile/non-volatile computer system storage media. By way of example only, storage system 914 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 906 may include at least one program product having a set (e.g., at least one) of program modules that are configured to carry out the functions of various embodiments of the application.

Program/utility 916, having a set (at least one) of program modules 918, may be stored in memory 906 by way of example, and not limitation, as well as an operating system, one or more application programs, other program modules, and program data. Each of the operating system, one or more application programs, other program modules, and program data or some combination thereof, may include an implementation of a networking environment. Program modules 918 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 902 may also communicate with one or more external devices 920 such as a keyboard, a pointing device, a display 922, etc.; one or more devices that enable a user to interact with computer system/server 902; and/or any devices (e.g., network card, modem, etc.) that enable computer system/server 902 to communicate with one or more other computing devices. Such communication can occur via I/O interfaces 924. Still yet, computer system/server 902 can communicate with one or more networks such as a local area network (LAN), a general wide area network (WAN), and/or a public network (e.g., the Internet) via network adapter 926. As depicted, network adapter 926 communicates with the other components of computer system/server 902 via a bus. It should be understood that although not shown, other hardware and/or software components could be used in conjunction with computer system/server 902. Examples include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. An apparatus, comprising:
   a processor that, when executing instructions stored in an associated memory, is configured to:
   extract a data object from a machine-readable code, where the data object comprises a first field of data that is signed with a digital signature of a private key and a second field of data that is hashed before being signed with the digital signature so that a value of the second field is not disclosed when the second field is verified,
   retrieve an identifier of an issuer of the data object from the data object,
   retrieve a public key from a blockchain based on the identifier of the issuer,
   verify the digital signature of the private key based on the public key,
   verify that a schema identifier of the first field matches a schema identifier of a first stored schema on the blockchain,
   verify that a hash of a schema identifier of the second field matches a hash of a second schema identifier of a second stored schema on the blockchain, and
   verify that the data object is trustworthy based on both the verification of the digital signature and the verification of the schema identifiers.

2. The apparatus of claim 1, wherein the processor is further configured to:
   retrieve, from the data object, a schema identifier that identifies the schema, and
   identify that the schema matches the stored schema based on the schema identifier matching a stored schema identifier on the blockchain.

3. The apparatus of claim 1, wherein the data object comprises:
   a string value that includes data values from the fields concatenated together.

4. The apparatus of claim 1, wherein the processor is further configured to:
   scan a quick response code via an imaging device, where the quick response code comprises the data object encoded therein.

5. The apparatus of claim 1, wherein the processor is configured to:
   transmit, to a blockchain peer, a request comprising the identifier of the issuer of the data object, and
   receive, from the blockchain peer, the public key.

6. The apparatus of claim 1, wherein the data object comprises:
   a certificate of health issued by the issuer, the certificate of health comprising a test result, a user identifier, and a timestamp.

7. The apparatus of claim 1, wherein, when the processor retrieves the public key, the processor is further configured to:
   retrieve the public key from a registry stored in the blockchain, the registry including identities of a plurality of issuers and public keys of the plurality of issuers.

8. The apparatus of claim 1, wherein the processor is configured to:
   extract an identity of a user associated with and corresponding to the fields of data.

9. A method, comprising:
   extracting a data object from a machine-readable code, where the data object comprises a first field of data that is signed with a digital signature of a private key and a second field of data that is hashed before being signed with the digital signature so that a value of the second field is not disclosed when the second field is verified;
   retrieving an identifier of an issuer of the data object from the data object;
   retrieving a public key from a blockchain based on the identifier of the issuer;

verifying the digital signature of the private key based on the public key;

verifying that a schema identifier of the first field matches a schema identifier of a first stored schema on the blockchain;

verifying that a hash of a schema identifier of the second field matches a hash of a second schema identifier of a second stored schema on the blockchain; and verifying that the data object is trustworthy based on both the verification of the digital signature and the verification of the schema identifiers.

10. The method of claim 9, further comprising:

retrieving, from the data object, a schema identifier that identifies the schema; and identifying that the schema matches the stored schema based on the schema identifier matching a stored schema identifier on the blockchain.

11. The method of claim 9, wherein the data object comprises:

a string value including data values from the fields concatenated together.

12. The method of claim 9, wherein the extracting comprises:

scanning a quick response code via an imaging device, where the quick response code comprises the data object encoded therein.

13. The method of claim 9, wherein the retrieving the public key further comprises:

transmitting, to a blockchain peer, a request comprising the identifier of the issuer of the data object; and receiving, from the blockchain peer, the public key.

14. The method of claim 9, wherein the data object comprises:

a certificate of health issued by the issuer, the certificate of health comprising a test result, a user identifier, and a timestamp.

15. The method of claim 9, wherein the retrieving the public key further comprises:

retrieving the public key from a registry stored in the blockchain, the registry including identities of a plurality of issuers and public keys of the plurality of issuers.

16. The method of claim 9, wherein the extracting further comprises:

extracting an identity of a user associated with and corresponding to the fields of data.

17. A computer program product comprising a non-transitory computer-readable medium storing instructions that, when executed by a processor, cause the processor to perform:

extracting a data object from a machine-readable code, where the data object comprises a first field of data that is signed with a digital signature of a private key and a second field of data that is hashed before being signed with the digital signature so that a value of the second field is not disclosed when the second field is verified;

retrieving an identifier of an issuer of the data object from the data object;

retrieving a public key from a blockchain based on the identifier of the issuer;

verifying the digital signature of the private key based on the public key;

verifying that a schema identifier of the first field matches a schema identifier of a first stored schema on the blockchain;

verifying that a hash of a schema identifier of the second field matches a hash of a second schema identifier of a second stored schema on the blockchain; and verifying that the data object is trustworthy based on both the verification of the digital signature and the verification of the schema identifiers.

18. The computer program product of claim 17, wherein the instructions further cause the processor to perform:

retrieving, from the data object, a schema identifier that identifies the schema; and identifying that the schema matches the stored schema based on the schema identifier matching a stored schema identifier on the blockchain.

19. The computer program product of claim 17, wherein the data object comprises:

a string value including data values from the fields concatenated together.

20. The computer program product of claim 17, wherein the extracting comprises:

scanning a quick response code via an imaging device, where the quick response code comprises the data object encoded therein.

* * * * *